(12) United States Patent
Maschino et al.

(10) Patent No.: US 7,835,796 B2
(45) Date of Patent: Nov. 16, 2010

(54) WEIGHT LOSS METHOD AND DEVICE

(75) Inventors: Steven E. Maschino, Seabrook, TX (US); Steven M. Parnis, Pearland, TX (US); Scott A. Armstrong, Danbury, TX (US)

(73) Assignee: Cyberonics, Inc., Houston, TX (US)

( * ) Notice: Subject to any disclaimer, the term of this patent is extended or adjusted under 35 U.S.C. 154(b) by 567 days.

(21) Appl. No.: 11/118,452

(22) Filed: Apr. 29, 2005

(65) Prior Publication Data

US 2006/0247719 A1    Nov. 2, 2006

(51) Int. Cl.
*A61N 1/00* (2006.01)
(52) U.S. Cl. ..................................... 607/40
(58) Field of Classification Search ............. 607/40, 607/116, 118, 133, 62
See application file for complete search history.

(56) References Cited

U.S. PATENT DOCUMENTS

| | | |
|---|---|---|
| 4,459,989 A | 7/1984 | Borkan |
| 4,592,339 A | 6/1986 | Kuzmak et al. |
| 4,612,934 A | 9/1986 | Borkan |
| 4,793,353 A | 12/1988 | Borkan |
| 5,003,975 A | 4/1991 | Hafelfinger et al. |
| 5,074,868 A | 12/1991 | Kuzmak |
| 5,188,104 A | 2/1993 | Wernicke et al. |
| 5,226,429 A | 7/1993 | Kuzmak |
| 5,231,988 A | 8/1993 | Wernicke et al. |
| 5,263,480 A | 11/1993 | Wernicke et al. |
| 5,411,528 A | 5/1995 | Miller et al. |
| 5,423,872 A | 6/1995 | Cigaina |

(Continued)

FOREIGN PATENT DOCUMENTS

WO    2004069330 A1    8/2004

(Continued)

OTHER PUBLICATIONS

Kriwanek, "*Therapeutic Failures After Gastric Bypass Operations for Morbid Obesity*," Langenbecks Archiv. Fur Chirurgie, 38(2): 70-74, 1995.

(Continued)

*Primary Examiner*—Mark W Bockelman
(74) *Attorney, Agent, or Firm*—Conley Rose, P.C.; Timothy L. Scott

(57) ABSTRACT

A method and apparatus for treatment of an eating disorder includes electrically, mechanically and/or pharmaceutically/chemically stimulating a of the vagus nerve of the lower esophagus, cardia, esophageal/cardia junction, cardia/fundus junction or upper stomach so as to induce afferent action potentials on the vagus nerve. The device may be noninvasively adjusted after implantation to provide increased or decreased restriction on the patient's gastrointestinal tract. Each stimulus may be administered as a series of programmed pulses of defined amplitude, duration and period, to evoke a responsive signal to the brain by the target nerve, effective for producing a temporary feeling of satiety in the person. An implantable stimulus generator may be operatively coupled to a nerve electrode, pressure device or chemical outlet to apply a defined signal to a selected nerve branch. The implantable stimulus generator is programmable to allow clinician programming of defined signal parameters effective to treat the eating disorder of the patient. Methods are also provided to identify electrodes nearest to a branch of the vagus nerve to apply an electrical stimulation signal with improved efficiency.

25 Claims, 7 Drawing Sheets

U.S. PATENT DOCUMENTS

| | | |
|---|---|---|
| 5,514,175 A | 5/1996 | Kim et al. |
| 5,534,018 A | 7/1996 | Wahlstrand et al. |
| 5,540,730 A | 7/1996 | Terry, Jr. et al. |
| 5,540,734 A | 7/1996 | Zabara |
| 5,601,604 A | 2/1997 | Vincent |
| 5,690,691 A | 11/1997 | Chen et al. |
| 5,771,903 A | 6/1998 | Jakobsson |
| 5,792,210 A | 8/1998 | Wamubu et al. |
| 5,836,994 A | 11/1998 | Bourgeois |
| 5,861,014 A | 1/1999 | Familoni |
| 5,919,216 A | 7/1999 | Houben et al. |
| 5,995,872 A | 11/1999 | Bourgeois |
| 6,009,877 A | 1/2000 | Edwards |
| 6,026,326 A | 2/2000 | Bardy |
| 6,041,258 A | 3/2000 | Cigaina et al. |
| 6,044,846 A | 4/2000 | Edwards |
| 6,083,249 A | 7/2000 | Familoni |
| 6,091,992 A | 7/2000 | Bourgeois et al. |
| 6,092,528 A | 7/2000 | Edwards |
| 6,097,984 A | 8/2000 | Douglas |
| 6,102,922 A | 8/2000 | Jakobsson et al. |
| 6,104,955 A | 8/2000 | Bourgeois |
| 6,115,635 A | 9/2000 | Bourgeois |
| 6,129,685 A | 10/2000 | Howard |
| 6,216,039 B1 | 4/2001 | Bourgeois |
| 6,321,124 B1 | 11/2001 | Cigaina |
| 6,327,503 B1 | 12/2001 | Familoni |
| 6,418,348 B1 | 7/2002 | Witte |
| 6,449,512 B1 | 9/2002 | Boveja |
| 6,450,173 B1 | 9/2002 | Forsell |
| 6,473,653 B1 | 10/2002 | Schallhorn et al. |
| 6,477,417 B1 | 11/2002 | Levine |
| 6,510,332 B1 | 1/2003 | Greenstein |
| 6,532,388 B1 | 3/2003 | Hill et al. |
| 6,535,764 B2 | 3/2003 | Imran et al. |
| 6,542,776 B1 | 4/2003 | Gordon et al. |
| 6,564,101 B1 | 5/2003 | Zikria |
| 6,587,719 B1 | 7/2003 | Barrett et al. |
| 6,587,726 B2 | 7/2003 | Lurie et al. |
| 6,591,137 B1 | 7/2003 | Fischell et al. |
| 6,594,524 B2 | 7/2003 | Esteller et al. |
| 6,600,953 B2 | 7/2003 | Flesler et al. |
| 6,606,523 B1 | 8/2003 | Jenkins |
| 6,609,025 B2 | 8/2003 | Barrett et al. |
| 6,609,031 B1 | 8/2003 | Law et al. |
| 6,610,713 B2 | 8/2003 | Tracey |
| 6,611,715 B1 | 8/2003 | Boveja |
| 6,615,081 B1 | 9/2003 | Boveja |
| 6,615,084 B1 | 9/2003 | Cigaina |
| 6,662,053 B2 | 12/2003 | Borkan |
| 6,684,104 B2 | 1/2004 | Gordon et al. |
| 6,754,536 B2 | 6/2004 | Swoyer et al. |
| 6,775,573 B2 | 8/2004 | Schuler et al. |
| 6,826,428 B1 | 11/2004 | Chen et al. |
| 6,832,114 B1 | 12/2004 | Whitehurst et al. |
| 6,853,862 B1 | 2/2005 | Marchal et al. |
| 6,889,076 B2 | 5/2005 | Cigaina |
| 6,895,278 B1 | 5/2005 | Gordon |
| 6,907,293 B2 * | 6/2005 | Grill et al. .................. 607/39 |
| 6,908,487 B2 | 6/2005 | Cigaina |
| 7,167,750 B2 * | 1/2007 | Knudson et al. ............... 607/40 |
| 7,310,557 B2 * | 12/2007 | Maschino et al. ............. 607/40 |
| 2001/0011543 A1 | 8/2001 | Forsell |
| 2003/0208212 A1 | 11/2003 | Cigaina |
| 2004/0015205 A1 | 1/2004 | Whitehurst |
| 2004/0167583 A1 | 8/2004 | Knudson |
| 2004/0172085 A1 | 9/2004 | Knudson |
| 2004/0176812 A1 | 9/2004 | Knudson |
| 2005/0010265 A1 * | 1/2005 | Baru Fassio et al. .......... 607/48 |
| 2005/0038484 A1 | 2/2005 | Knudson |
| 2005/0049655 A1 | 3/2005 | Boveja |
| 2005/0070974 A1 * | 3/2005 | Knudson et al. ............... 607/58 |
| 2005/0131485 A1 | 6/2005 | Knudson |
| 2005/0131486 A1 | 6/2005 | Boveja |
| 2005/0149142 A1 | 7/2005 | Starkebaum |
| 2005/0192644 A1 | 9/2005 | Boveja |
| 2006/0173238 A1 | 8/2006 | Starkebaum |
| 2006/0189887 A1 | 8/2006 | Hassler, Jr. |

FOREIGN PATENT DOCUMENTS

| | | |
|---|---|---|
| WO | 2005007232 A2 | 1/2005 |

OTHER PUBLICATIONS

Grundy et al., "Sensory Afferents From the Gastrointestinal Tract," Chapter 10, Handbook of Physiology, Sec. 6, S.C., Ed., American Physiology Society, Bethesda, Md., 1989.

"A Protective Role for Vagal Afferents: An Hypothesis," Neuroanatomy and Physiology of Abdominal Vagal Afferents, Chapter 12, CRC Press, New York, NY, 1992.

"External Sensory Events and the Control of the Gastrointestinal Tract: An Introduction," Neuroanatomy and Physiology of Abdominal Vagal Afferents, Chapter 5, CRC Press, New York, NY, 1992.

Neuroanatomy and Physiology of Abdominal Vagal Afferents, Ch. 10 Ritter, Ritter and Barnes, Ed., CRC Press, 1992.

Leibowitz, Eating Disorders and Obesity, A Comprehensive Handbook, Ch. 1, Brownell and Fairburn, Ed., The Guilford Press, 1995.

Woodbury et al., Vagal Stimulation Reduces the Severity of Maximal Electroshock Seizures in Intact Rats: Use of a Cuff Electrode for Stimulating and Recording. Pacing and Clinical Electrophysiology, vol. 14 (Jan. 1991), pp. 94-107.

Zabara, Jacob, Inhibition of Experimental Seizures in Canines by Repetitive Vagal Stimulation, Epilepsia, vol. 33(6) (1992), pp. 1005-1012.

Henry, Thomas R., Therapeutic Mechanisms of Vagus Nerve Stimulation, Neurology, vol. 59 (Supp. 4) (Sep. 2002), pp. S3-S14.

Lockard et al., Feasibility and Safety of Vagal Stimulation in Monkey Model, Epilepsia, vol. 31 (Supp. 2) (1990), pp. S20-S26.

Hallowitz et al., Effects of Vagal Volleys on Units of Intralaminar and Juxtalaminar Thalamic Nuclei in Monkeys, Brain Research, vol. 130 (1977), pp. 271-286.

Bachman et al., Effects of Vagal Volleys and Serotonin on Units of Gulate Cortex in Monkeys, Brain Research, vol. 130 (1977), pp. 253-269.

Terry et al., The Implantable Neurocybernetic Prosthesis System, Pacing and Clinical Electrophysiology, vol. 14, No. 1 (Jan. 1991), pp. 86-93.

Vonck et al., The Mechanism f Action of Vagus Nerve Stimulation for Refractory Epilepsy, Journal of Clinical Neurophysiolgy, vol. 18(5) (2001), pp. 394-401.

* cited by examiner

WEIGHT LOSS METHOD AND DEVICE

CROSS-REFERENCE TO RELATED APPLICATIONS

The present invention is a related application to U.S. patent application Ser. No. 11/118,980, entitled "Noninvasively Adjustable Gastric Band," and U.S. patent application Ser. No. 11/118,861, now U.S. Pat. No. 7,310,557, entitled "Identification of Electrodes for Nerve Stimulation In the Treatment of Eating Disorders." Both applications are filed on the same date as the present application and in the name of same inventors.

BACKGROUND OF THE INVENTION

1. Field of the Invention

The present invention generally relates to apparatus and methods for treatment of eating disorders, such as obesity, bulimia nervosa, and anorexia nervosa, and more particularly to treatments and therapies which employ vagus nerve stimulation in the esophageal/gastric area of the body in conjunction with gastric restriction.

2. Description of Related Art

Increasing prevalence of obesity is one of the most serious and widespread health problems in the world. It is estimated that about 6% of the current population of the United States is morbidly obese, defined as having a body mass index of more than forty, or as is more commonly understood, being more than one hundred pounds overweight for a person of average height. In addition to the morbidly obese, a much larger percentage of the population is either obese or significantly overweight. Aside from what may be an epidemic of obesity, it is believed by some health experts that obesity is one of the first two leading causes of preventable deaths in the United States, either ahead of or just behind cigarette smoking.

The classical treatment regimen for obese persons, which combines nutritional counseling with exercise and education, has demonstrated relatively little long term success. In general, liquid diets and pharmaceutical agents can bring about acute, but rarely lasting, weight loss. Surgery to provide either gastric restriction or malabsorption in cases of severe obesity have shown the greatest success long-term, but are major surgical procedures that can lead to emotional problems, and which have their share of failures (see, e.g., Kriwanek, "Therapeutic failures after gastric bypass operations for morbid obesity," *Langenbecks Archiv. Fur Chirurgie*, 38(2): 70-74, 1995).

Among the surgical approaches to the treatment of morbid obesity, various stomach banding or gastroplasty ring devices have been employed for gastric restriction (i.e., decreasing the size of the stomach) to reduce food intake. For example, U.S. Pat. No. 4,592,339 (Mentor Corporation), U.S. Pat. Nos. 5,074,868, 5,226,429 and 5,601,604 (Inamed Development Co.) and U.S. Pat. Nos. 5,771,903 and 6,102,922 (Kirk Promotions Limited). Some of the known gastric bands have incorporated an inflatable member for adjusting the diameter of the stoma opening created by the band.

There have also been efforts to treat obesity, and syndromes related to motor disorders of the stomach of a patient, by altering natural gastric motility of the patient. For example, U.S. Pat. No. 5,423,872 (Cigaina) identifies a "gastric pacemaker" region of the stomach, at a point proximate to the greater curvature, at which propulsive gastric movements begin and from which electrical pulses (depolarization potential) spread in an anterograde direction along the entire stomach. The patent describes a process of altering, by means of sequential electrical pulses and for preset periods of time, the natural gastric motility of a patient and/or the time and manner of contraction of the lower esophageal and pyloric sphincters to prevent emptying (or to slow down) gastric transit, to prevent duodenal acidification during interdigestive phases, or to prevent gastric reflux in the last portion of the esophagus. The stimulator device is placed subcutaneously in the abdominal wall and is connected to the distal gastric antrum by means of an electrocatheter.

U.S. Pat. No. 5,690,691 (The Center for Innovative Technology) describes an implantable or portable gastrointestinal pacemaker for any organ in the gastro-intestinal tract through which peristaltic movement of material is controlled by natural electrical pacing, and includes multiple electrodes that are positionable at multiple sites on a single organ or on different sites on different organs. Feedback from the gastrointestinal tract can be provided by one or more sensor electrodes.

U.S. Pat. App. Pub. No. 2003/0208212 (Cigaina) describes a removable gastric band which may be paired with the use of a gastric electrostimulator for inducing forced slimming in the initial phase of treatment for morbigenous obesity. Such electrostimulation devices may either be incorporated into the removable gastric band or located at a distance from the removable gastric band.

U.S. Pat. No. 6,510,332 (Transneuronix, Inc.) describes an implant device for electrostimulation and/or electrical monitoring of endo-abdominal tissue or viscera. In the background discussion of that patent it is said that stimulation of the intrinsic nervous system of the stomach is likely to have two major consequences or effects: (1) the correction and direct control of the electromotor activity of the intestines and (2) the stimulation of increased incretion of specific substances (i.e., gastroenteric neuromediators) produced by the intrinsic nervous system itself thorough the myenteric plexus.

In addition to electrical stimulation of gastrointestinal structures, treatment of eating disorders by stimulation of one or more cranial nerves, particularly the vagus nerve, is also known. U.S. Pat. No. 5,188,104 (Cyberonics, Inc.) describes methods and devices for stimulation of the vagus nerve to treat compulsive overeating and obesity, and other eating disorders such as bulimia and anorexia nervosa. In some procedures for treating obesity, the stimulating electrode is implanted about the vagus nerve or branch thereof in the esophageal region slightly above the stomach. Passage of food can be monitored via sensing electrodes as the patient swallows, and modulation of vagal activity may be initiated when a predetermined total amount of food has been consumed, when the patient perceives a need for treatment, according to circadian rhythms of the patient, or according to a schedule of preset time intervals.

U.S. Pat. No. 5,263,480 (Cyberonics, Inc.) describes treatment of obesity and compulsive overeating disorder by selectively applying modulating electrical signals to the patient's vagus nerve, preferably using an implanted neurostimulator. Modulating signals may be used to stimulate vagal activity to increase the flow of neural impulses up the nerve (i.e., afferent action potentials), or to inhibit vagal activity to block neural impulses from moving up the nerve, thereby producing excitatory or inhibitory neurotransmitter release. Both ways of modulating vagus nerve electrical activity have been termed vagus nerve stimulation (VNS).

The '480 patent describes the use of VNS for appetite suppression by causing the patient to experience satiety, which would result in decreased food consumption and consequent weight reduction. A pulse generator is implanted in a convenient location in the patient's body, attached to an electrical lead having a nerve electrode coupled to the vagus nerve (or a branch thereof) in the esophageal region slightly above the stomach. The pulse generator is triggered to apply VNS therapy and thereby reduce or eliminate the patient's appetite. VNS therapy may be applied periodically or intermittently during the patient's normal waking hours according to a preset duty cycle, such as thirty seconds on-time and five minutes off-time. In alternate embodiments, electrical stimulation may be provided as a continuous pulse train throughout the day except at mealtimes, and the patient may manually activate the stimulus generator by a variety of known methods such as placing an external magnet on the skin overlying the implanted stimulus generator, or by tapping the stimulus generator through the skin in the same area. See, e.g., U.S. Pat. No. 5,304,206. VNS may also be initiated if the patient's food consumption over a given period exceeds a predetermined threshold level, detected and measured for example by sensing electrodes implanted at or near the esophagus. Patient intervention assumes a patient with an earnest desire to control his or her eating behavior, but normally lacking sufficient willpower to control the compulsive behavior without the support of VNS therapy.

More recently, U.S. Pat. App. Pub. No. 2004/0167581 (Knudson et al.) describes a gastric band with electrodes for vagus nerve stimulation. This application is directed to treatment of functional dyspepsia, irritable bowel syndrome, gastroparesis, gastroesophageal reflux disease (GERD), by blocking intrinsic (i.e., natural) vagus nerve action potentials traveling along the nerve. To the extent that the '581 application is concerned with treating eating disorders, it is specifically intended to block native action potentials from traveling along the nerve, as opposed to inducing artificial afferent or efferent action potentials. See '581 application at paragraphs 150-155. Although blocking of certain native action potentials (i.e., at certain time periods) may be included within the scope of the present invention, in contrast to the aforementioned '581 application the present invention in preferred embodiments includes the generation of induced afferent and/or efferent action potentials on the vagus nerve, with or without blocking of native action potentials.

Notwithstanding the foregoing prior art, there remains a need for improved therapies and devices to provide gastric restriction and/or vagus nerve stimulation for treatment of eating disorders. Accordingly, it is an object of the present invention to provide improved methods and devices for combining gastric restriction with vagus nerve stimulation for the treatment of eating disorders. It is a further object of the present invention to provide improved methods and devices for the treatment of eating disorders by combining gastric restriction with vagus nerve stimulation for inducing afferent and/or efferent action potentials on the vagus nerve. It is a still further object of the invention to provide a gastric band for the treatment of eating disorders that may be adjusted after implantation into the patient's body. It is an additional object of the present invention to provide a gastric band that may be post-operatively and noninvasively adjusted by a physician using an external adjustment device after implantation of the band. It is another object of the present invention to provide a gastric band capable of both sensing and stimulating the vagus nerve. It is yet another object of the invention to provide improved methods and devices to minimize electrical energy usage in providing electrical stimulation of the vagus nerve for the treatment of eating disorders. It is another object of the present invention to use induced action potentials on the vagus nerve to determine which electrodes among a plurality of electrodes on a gastric band have the most effective electrical communication with the vagus nerve.

The Vagus Nerve

The vagus nerve, the tenth cranial nerve, originates from the brain stem, passing through foramina of the skull to parts of the head, neck and trunk. It is a mixed nerve, with both sensory and motor fibers, the sensory fibers being primary and attached to neuron cell bodies located outside the brain in ganglia groups, and the motor fibers attached to neuron cell bodies located within the gray matter of the brain. Somatic fibers of the cranial nerves are involved in conscious activities and connect the CNS (central nervous system) to the skin and skeletal muscles, while autonomic fibers of these nerves are involved in unconscious activities and connect the CNS to the visceral organs such as the heart, lungs, stomach, liver, pancreas, spleen, and intestines.

Motor fibers of the vagus nerve transmit impulses from the brain to the muscles associated with speech and swallowing, the heart, and smooth muscles of the visceral organs of the thorax and abdomen. In contrast, the vagus nerve's sensory fibers transmit impulses from the pharynx, larynx, esophagus and visceral organs of the thorax and abdomen to the brain. At the base of the brain, the vagus nerve branches into the left and right vagi, which run respectively through the left and right sides of the neck and trunk.

The vagus nerve, including both the right and left branches or vagi, is the dominant nerve enervating the gastrointestinal (GD) tract. After branching from the spinal cord, the vagal afferents transport information regarding the GI tract to the brain. In the lower part of the chest, the left vagus rotates anteriorly to become the anterior vagus, which innervates the stomach by branches distributed over its anterosuperior surface. Some of those branches extend over the fundus, and others along the lesser curvature of the stomach, as illustrated in simplified form in FIG. 6. The right vagus rotates to become the posterior vagus (not shown in FIG. 6), where it is distributed to the postero-inferior surface of the stomach, forming the celiac division, joining the left side of the celiac plexus, and innervating the duodenum and proximal intestinal tract.

While the vagus is often considered to be a motor nerve that also carries sensory signals, 80% of the individual nerve fibers are sensory afferent fibers (e.g., Grundy et al., "Sensory afferents from the gastrointestinal tract," Chapter 10, HANDBOOK OF PHYSIOLOGY, Sec. 6, S.G., Ed., American Physiology Society, Bethesda, Md., 1989). Afferent nerve impulses are conducted inwardly toward a nerve center, such as the brain or spinal cord, via afferent nerve fibers. Efferent nerve impulses are conducted outwardly or away from a nerve center along efferent nerve fibers, usually going to an effector to stimulate it and produce activity. Thus, for purposes of the present application, vagal afferent signals transmit sensory information to the brain from the gastrointestinal tract, and vagal efferent signals transmit motor signals from the brain to the GI tract.

The exact mechanisms leading an individual to experience a feeling of satiety or appetite reduction are not fully known, but a substantial amount of information has been accumulated and reported in the literature. Satiety signals include the stretch of mechanoreceptors and the stimulation of certain chemosensors ("A Protective Role for Vagal Afferents: An Hypothesis," NEUROANATOMY AND PHYSIOLOGY OF ABDOMINAL VAGAL AFFERENTS, Chapter 12, CRC Press, New York, N.Y., 1992). These signals are transported to the brain by the nervous system or endocrine factors such as gut peptides ("External Sensory Events and the Control of the Gastrointestinal Tract: An Introduction," id. at Chapter 5). It has been demonstrated that direct infusion of maltose and oleic acid into the duodenum of rats leads to a reduction in food intake, and that this reduced food consumption response is ablated by vagotomy or injection of capsaicin, which destroys vagal afferents. Introduction of systemic cholecystokinin also reduces food intake in rats, and is likewise ablated by destruction of vagal afferents. An accepted and well-researched hypothesis is that some vagal sensory information is used to control food intake. Experiments have shown that the gastrointestinal (GI) tract is the most likely source of signals contributing to the termination of eating (see, e.g., Neuroanatomy and Physiology of Abdominal Vagal Afferents, Ch. 10 Ritter, Ritter and Barnes, Ed., CRC Press, 1992 The predominant view is that, from the gastrointestinal tract, cholecystokinin and other peptides are released after a meal to coordinate several aspects of digestion, absorption, and metabolism and to transmit information to the brain, via the vagus nerve, that signals meal termination and satiety (see Leibowitz, Eating Disorders and Obesity, A Comprehensive Handbook, Ch. 1, Brownell and Fairburn, Ed., The Guilford Press, 1995). The left and right vagi, or anterior and posterior as they are called in the thoracic and GI area, selectively innervate various areas of the viscera such as the stomach and intestines. Stimulation of both vagi would insure that afferent (towards the brain) signals from all visceral organs are created.

U.S. Pat. No. 6,587,719 (Cyberonics, Inc.) describes a method of treating patients for obesity by bilateral stimulation of the patient's vagus nerve (i.e., bilateral VNS). A stimulating electrical signal, with parameters determined to induce weight loss, is applied to one or both branches of the vagus. The signal is preferably a pulsed signal applied according to a set duty cycle (i.e., on and off times) intermittently to both vagi. In any event, VNS is applied at a supra-diaphragmatic position (i.e., above the diaphragm) in the ventral cavity. The electrical pulse stimuli are set at a current magnitude below the retching level of the patient (e.g., not exceeding about 6 milliamperes (mA), to avoid patient nausea) in alternating periods of continuous application (via a train or series of electrical pulses) and no application. Pulse width is set at or below 500 microseconds ($\mu s$), and pulse repetition frequency at about 20-30 Hz. The on/off duty cycle (i.e., first period/second period of the alternating periods) is programmed to a ratio of about 1:1.8. The neurostimulator, which may be a single device or a pair of devices, is implanted and electrically coupled to lead(s) having nerve electrodes implanted on the right and left branches of the vagus.

U.S. Pat. No. 6,609,025 (Cyberonics, Inc.) describes a similar method of treating patients for obesity by unilateral or bilateral stimulation of either or both of the left and right vagi; however the electrical stimulation is applied at a sub-diaphragmatic position (i.e., below the diaphragm). It is theorized that sub-diaphragmatic stimulation may provide an enhanced effect in inducing a feeling of satiety because it is administered in closer proximity to the stomach itself.

BRIEF SUMMARY OF THE INVENTION

Apparatus and methods for treating obesity are provided which constitute improvements over prior surgical obesity treatments by providing a way to induce appetite reduction and desirable weight loss in the obese patient. Improved treatments for other eating disorders are also provided. Improved methods of treating bulimia nervosa are provided to reduce voluntary and/or involuntary purging following consumption of food. Methods of the invention generally include electrically, mechanically, or chemically stimulating an anterior and/or posterior branch of the vagus nerve of the lower esophagus, cardia, esophageal/cardia junction, cardia/fundus junction or upper stomach. Stimulation is delivered via electrical, mechanical or chemical stimulation elements, respectively, coupled to a gastric band that is in turn coupled to the esophagus and/or stomach.

As used herein, "stimulation" of a nerve refers to the delivery of a stimulus to the nerve. The stimulus may be an electrical, mechanical, or chemical stimulus. Stimulation includes delivery of stimuli to generate exogenous (i.e., artificial) action potentials in one or more fibers of the nerve bundle, as well as stimuli incapable of generating an action potential and which are delivered for another purpose, such as blocking endogenous (i.e., native) action potentials from continuing on the nerve. "Modulation" may be used interchangeably with "stimulation" and refers to the effects of a stimulus on the neural impulses traveling on the nerve, which may include blocking native action potentials or generating exogenous action potentials.

Embodiments of the present invention may involve delivery of stimulation to the vagus nerve at programmed time intervals (e.g., every five minutes) without regard to the physical condition of the patient, time of day, or other variables that may influence the need for, and/or efficacy of, the stimulation. This type of stimulation is referred to as "passive stimulation." Other embodiments of the invention may involve stimulation of the vagus nerve in response to the detection of a physiological event or upon another occurrence such as a normal mealtime of the patient. Such responsive stimulation is referred to as "active stimulation."

The term "chemical" is intended to include both stimulatory and therapeutic agents, including drugs or pharmaceuticals and chemicals. For example, a "chemical" could be a nerve excitatory chemical or it could be an antibiotic, as the context allows.

Regardless of whether the stimulation employed is electrical, mechanical, chemical, or a combination stimulation modes, the stimulation may be administered as a series of programmed pulses of defined parameters. For electrical stimulation, the defined parameters may comprise current amplitude, pulse width, frequency, and on/off duty cycle, for a defined length of time and/or at defined intervals. Preferred vagus nerve stimulation (VNS) treatments of the present invention evoke a responsive afferent signal on the vagus nerve that is delivered to the brain to treat the eating disorder. Although a single stimulation program has been described, it will be understood that two or more programs (having different stimulation parameters) may operate sequentially, at programmed times during the patient's circadian rhythm, or at different times during a repeating program cycle.

In one aspect, the invention comprises systems and methods for treating an eating disorder with a gastric band and vagus nerve stimulation sufficient to induce afferent and/or efferent action potentials on the vagus nerve. Eating disorders suitable for treatment in the present invention include obesity and compulsive eating to excess, bulimia, and anorexia nervosa. In one embodiment of this aspect of the invention, a system is provided for treating an eating disorder by electrical stimulation of a vagus nerve in a manner to induce an afferent action potential on the nerve. The system comprises an implantable gastric band contacting the patient's gastrointestinal tract, and a pulse generator coupled to electrodes on the inner surface of the band for providing an electrical signal sufficient to induce afferent action potentials on the patient's vagus nerve. The pulse generator is preferably an implantable pulse generator, although an external, RF-coupled pulse generator may alternatively be provided.

In another embodiment, the invention comprises a method of treating an eating disorder by inducing afferent action potentials on the vagus nerve with an electrical stimulation signal. The method comprises surgically coupling a gastric band having electrodes thereon to a vagus nerve on the patient's GI tract, and providing an electrical signal to one or more of those electrodes sufficient to induce afferent action potentials, on the vagus nerve. The electrical signal is preferably used to stimulate both afferent and efferent signals on both the anterior and posterior vagus nerves.

Gastric bands used in the invention may be adjustable, preferably by non-invasive means such as an RF signal, to provide a variable constriction or constrictive force to the patient's gastrointestinal tract. The gastric band preferably includes both sensing and stimulation electrodes, with the sensing electrodes being used for detecting induced afferent action potentials on the nerve and to identify which stimulation electrodes are nearest to the vagus nerve. Electrical signals delivered to the vagus nerve are preferably pulsed electrical signals defined by current, frequency, pulse width, on-time and off-time.

Embodiments of this and other aspects of the invention may also comprise mechanical and/or chemical stimulation controllers and elements for providing mechanical and/or chemical stimulation of the patient's vagus nerve.

In another aspect, the invention comprises systems and methods for noninvasively adjusting a gastric band for treatment of eating disorders. In one embodiment, the invention comprises a method for noninvasively adjusting a surgically implanted gastric band having an adjustment element. An adjustment signal for actuating the adjustment element may be transmitted by an external adjustment controller to a receiver coupled to the adjustment element. The adjustment element may comprise an adjustable clamp, a worm gear, or one or more expandable balloon elements.

In another embodiment, the invention comprises a noninvasively adjustable gastric band system for treating an eating disorder. The system includes an implantable gastric band to engaging the patient's GI tract, an adjustment element coupled to the band, a receiver for receiving an adjustment signal, and an external adjustment controller for generating and transmitting the adjustment signal.

Adjustable gastric bands in this aspect of the invention also preferably comprise a plurality of stimulation and sensing electrodes for stimulating and sensing afferent and efferent action potentials on the anterior and posterior vagus nerve branches. A pulse generator, which may be implantable or external, is also preferably provided to generate the stimulation and sensing electrical signals. The electrical stimulation signals are preferably defined by a plurality of stimulation parameters such as current magnitude, frequency, pulse width, on-time and off-time.

Adjustments to the adjustable gastric band may be made by a computer algorithm, which may adjust the constriction of the gastric band according to the patient's circadian rhythms, time of day, to maintain a constant pressure on the GI tract as measured by a pressure sensor, or according to the wishes of a physician or the patient. In the latter case, suitable limits are preferably placed on the constriction that may be provided.

In a still further aspect, the invention provides systems and methods for selecting which electrodes, from among a plurality of electrodes on a gastric band, for use in providing electrical stimulation to the patient's vagus nerve to treat an eating disorder. Providing a therapeutic electrical signal to electrodes not in contact with the vagus nerve constitutes a waste of energy and will cause early power supply failure. Gastric bands of the invention may be provided with a plurality of sensing and stimulation electrodes, each of which provides an address identifying its location on the band. In preferred embodiments, the sensing and stimulation electrodes are different electrodes, but a single group of electrodes may also be used for both stimulation and sensing. After the band is surgically coupled to the patient's GI tract, a test signal capable of inducing an action potential on the vagus nerve is provided to a stimulation electrode. The sensing electrodes are then used to determine whether or not an action potential was induced by the stimulation, and if an action potential is detected the location of the nearest stimulation electrode is noted from the electrode addresses.

In certain embodiments, the stimulation electrodes may simultaneously be energized by the stimulation test signal, and individual sensing electrodes are then used to attempt to detect any induced action potential. In other embodiments, individual stimulation electrodes may be energized by the stimulation test signal, and all of the sensing electrodes may be used to determine whether the stimulation electrode induced a vagus nerve action potential. In either instances, the location of the stimulation electrode(s) nearest to the sensing electrode(s) detecting the action potential are used to identify stimulation electrodes for subsequently delivering a therapeutic stimulation signal.

While the method of identifying electrodes near the vagus nerve may be used immediately following surgery, it may also be repeated periodically to ensure that electrical contact with the vagus nerve is maintained. Movement of the band relative to the GI tract, or more likely, movement of the GI tract relative to the band, can effectively shut off electrical contact between the identified electrodes and the vagus nerve. Repeating the method may re-establish electrical contact with the vagus nerve.

In another embodiment, a system for providing selective electrical stimulation of electrodes in contact with a vagus nerve of the patient's GI tract is provided to treat eating disorders. The system includes an implantable gastric band with a plurality of stimulation electrodes and a plurality of sensing electrodes, each of having a unique address identifying its position on the band. An implantable pulse generator is provided for generating an electrical test signal and a therapeutic signal for delivery to selected electrodes. A testing and stimulation controller includes a testing algorithm that causes the pulse generator to generate and apply the test signal to the stimulating electrodes, and to sense for an induced action potential using the sensing electrodes. The controller also notes which sensing electrodes have sensed an induced vagus nerve action potential and identifies the stimulation electrodes nearest to those sensing electrodes. The controller preferably includes a therapeutic algorithm which used the identified stimulation electrodes to apply a therapeutic electrical signal to the vagus nerve.

An external controller is preferably provided for programming the testing and therapeutic algorithms. Systems and methods of this aspect of the invention may also incorporate wireless adjustment of the gastric band. The external controller may be used for this purpose, as well as to automatically or manually repeat the testing algorithm periodically or on command.

These and other embodiments, features and advantages will be apparent with reference to the drawings and description which follow.

BRIEF DESCRIPTION OF THE DRAWINGS

In FIG. 7 the band encircles the lower esophagus/upper cardia. In FIG. 8 the band encircles the central cardia region. In FIG. 9 the band spans the lower cardia and fundus regions, and encompasses the uppermost portion of the body of the stomach.

DETAILED DESCRIPTION OF THE PREFERRED EMBODIMENTS

Figure 1:
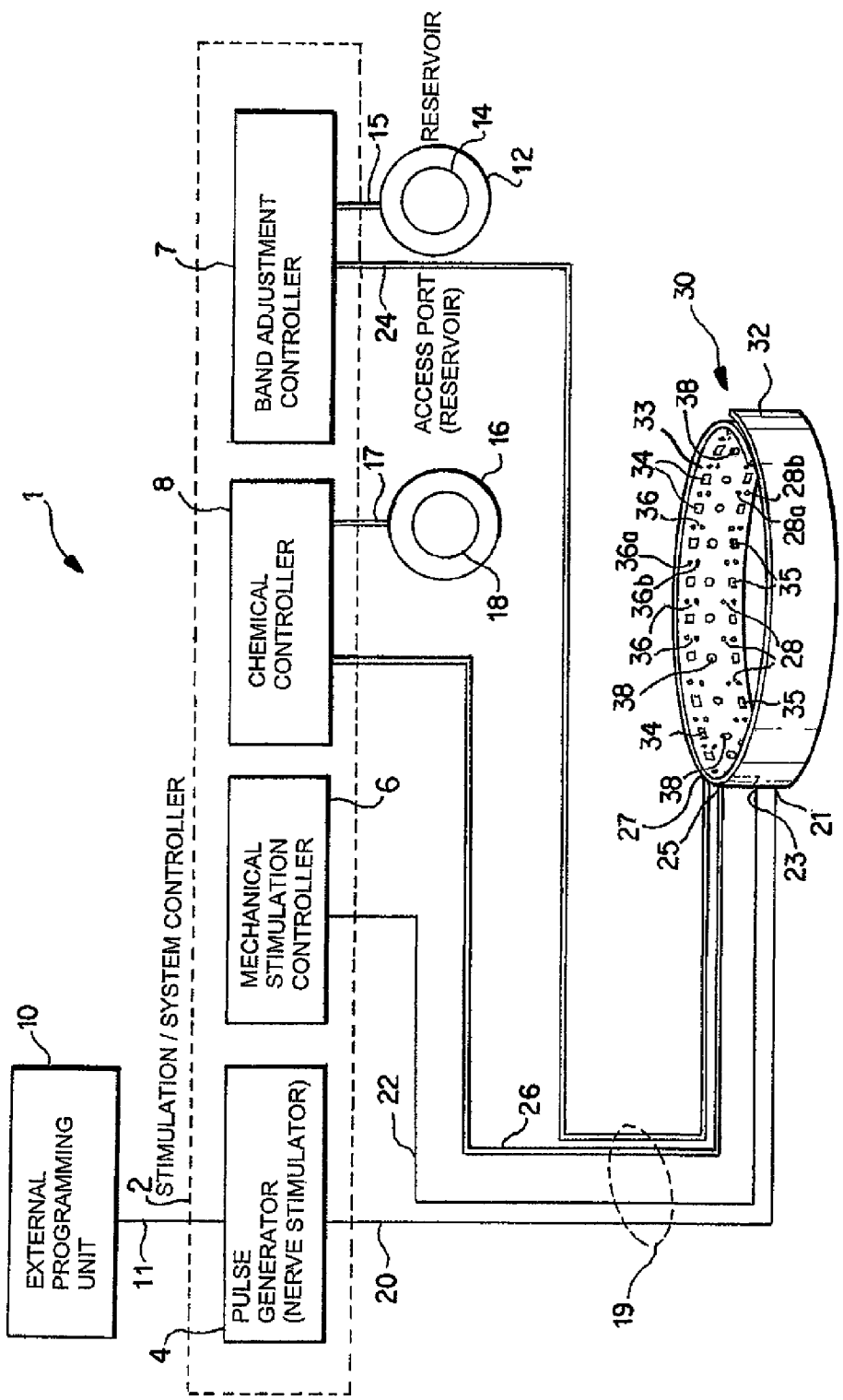
FIG. 1 is a block diagram of one embodiment of a treatment system of the present invention comprising an external programming unit, an implantable gastric band containing a plurality of stimulus elements, an implantable stimulation controller, electrical leads, and tubing and fluid reservoirs. The stimulation controller comprise a pulse generator, a mechanical stimulation controller, a chemical controller, and a band adjustment controller.

The following description and examples are offered by way of illustration, and not by way of limitation. Persons of skill in the art will recognize that many variations of the exemplified embodiments can be made, especially in light of the teachings of the various references cited herein, the disclosures of which are hereby incorporated by reference herein.

Systems of the present invention generally comprise a gastric band for encircling a region of the gastrointestinal tract, preferably at or near the cardia of the stomach, and an implantable neuromodulation controller comprising one or more implantable sub-units capable of modulating electrical activity on a vagus nerve of the patient and/or changing a constriction applied to a gastric structure. An external programming unit or programming module is also preferably included. The term "gastric band" is intended to include bands that are capable of looping around or encircling at least a portion of the lower esophagus, cardia, esophageal-cardia junction, cardia-fundus junction or upper portion of the stomach (i.e., areas that are innervated by the left or right vagus nerves or branches thereof) for restricting the volume of one or more of the aforementioned structures. In one embodiment, the external programming unit comprises a processor capable of receiving sensed information from the implantable stimulation controller, analyzing the information, and developing or changing a therapeutic algorithm to provide regulatory signals or programming to one or more of the stimulation units of the implantable stimulation controller.

Referring to FIGS. 1-5 and 7-9, band 30 is preferably capable of forming an adjustable loop around an esophageal/upper stomach area. The band may be adjusted in circumference so as to constrict the diameter of the encircled area, thereby creating a small gastric pouch to limit and control the amount of food that is eaten, and slowing the emptying process from the stomach into the intestines by creating a smaller entrance (stoma) to the body of the stomach. After band 30 is carefully positioned, the diameter is adjusted, and the band is preferably fixed to the outside of the stomach wall to prevent migration. This may be accomplished by sutures or by using another suitable technique or fixation device as is known in this field for securing conventional gastric bands. When band 30 is properly placed for treating an eating disorder, the therapeutic operation of assembly 1 should not appreciably alter normal peristalsis, and should not provoke vomiting or a sensation of gagging or choking in the patient. In one embodiment, the vagus nerve is stimulated to reduce the patient's appetite and/or desire to eat as a treatment for obesity. In another embodiment, the vagus nerve is stimulated to reduce purging behavior and thereby treat bulimia.

New treatment systems for obese patients may comprise gastric constriction combined with one or more of three different modalities for modulating electrical activity on the vagus/gastric nerves of the lower esophagus and upper stomach, i.e., an electrical mode, a mechanical mode and a chemical mode. In the representative assembly schematically illustrated in FIG. 1, all three modulation modalities are shown to provide one, two or all three types or modes of vagus nerve stimuli at one or more application sites within a single treatment area (i.e., tissue surrounded by a gastric band). The treatment assembly may be programmed to operate any one of the stimulation modalities alone, or in any combination of modalities, either independently or in concert, in accordance with the particular needs of the patient.

In treatment system employing electrical modulation of the vagus nerve, new methods to determine which electrodes from among a plurality of electrodes should be used to provide the electrical stimulation signal. In particular, sensing electrodes may be employed in combination with stimulating electrodes to identify which of the stimulating electrodes induce the largest action potential signal on one or both of the anterior and posterior vagus nerves. Several algorithms may be employed to identify which of the stimulating electrodes provide the most effective modulation of the vagus nerve.

Certain embodiments of the present invention also permit noninvasive, in situ adjustment of a gastric band by an external band adjustment controller after the band is implanted in the body of the patient. Such a band allows a healthcare provider or the patient to post-operatively and noninvasively adjust the gastric restriction provided by the band as needed or desired, without further surgical intervention into the body of the patient. In one embodiment, the band is automatically adjusted according to a treatment algorithm to maintain a relatively constant pressure on a gastric structure, without the need for intervention from a healthcare provider. FIG. 1 also depicts a band adjustment controller and fluid reservoir for adjusting the degree of constriction provided by the gastric band.

Referring to FIG. 1, treatment system 1 for treating an obese person comprises a gastric band 30 and an implantable system controller 2 which comprises a number of modulation sub-units, including a pulse generator 4, a mechanical modulation (or stimulation) controller 6, a chemical modulation controller 8, and a band adjustment controller 7. A group 19 of interconnecting electrical leads 20, 22 and tubes 24, 26 couples the sub-units 4, 6., 8 and 7 of system controller 2 to band 30 at connectors 21, 23, 27 and 25, respectively. Mechanical stimulation elements 34 are provided for applying mechanical pressure to the vagus nerve at a desired frequency in response to a signal from pressure controller 6. One or more power supplies (not shown), such as a conventional long-lasting implantable medical device battery, or set of batteries, is preferably included in stimulation controller 2, for powering the sub-controllers 4, 6, 8 and 7. A fluid reservoir 12 is provided for adjusting the constriction of the band 30 on the esophagus and/or stomach. Reservoir 12 is coupled to band adjustment controller 7 by a conduit or tube 15. A chemical reservoir 16 is available for providing chemical stimulation, coupled to chemical controller 8 by conduit or tube 17. An external programming unit 10 is provided for programming and receiving data from the system controller (or sub-units thereof). Gastric band 30 comprises an inner surface 33 for surrounding and contacting an outer surface of the stomach or esophagus. Electrodes 36 (for electrical stimulation), sensors (electrodes 28 and pressure sensors 35), vibration elements 34 (for mechanical stimulation), and outlet ports 38 (for chemical stimulation) are coupled to gastric band 30, preferably on inner surface 33. Preferably electrodes 36 comprise a plurality of electrode pairs 36a,36b, and sensing electrodes 28 comprise a plurality of electrode pairs 28a, 28b.

It will be appreciated that body 32 of band 30 is illustrated in FIG. 1 in a simplified, schematic form, and that many known gastric band designs can be readily modified to provide a band 30 suitable for use in the present invention. When closed to form a loop (which may be a complete loop or a partial loop) around an area of the lower esophagus and/or upper stomach region, the circumference of body 32 is preferably capable of being post-operatively and non-invasively adjusted in situ, as described more fully hereinafter. Band 30 may be implanted and removed during either open or, more preferably, minimally invasive surgical procedures (e.g., laparoscopically). Body 32 is preferably flexible and in a preferred embodiment comprises silicone. However, any suitable known gastroplasty band design may be adapted for use as band 30. One such design is a conventional LAP-BAND®, commercially available from Inamed Health, Santa Barbara, Calif. Other examples of adaptable band designs are those described in U.S. Pat. App. Pub. No. 2003/0208212 and U.S. Pat. No. 6,102,922, the disclosures of which are hereby incorporated herein by reference.

Figure 2:
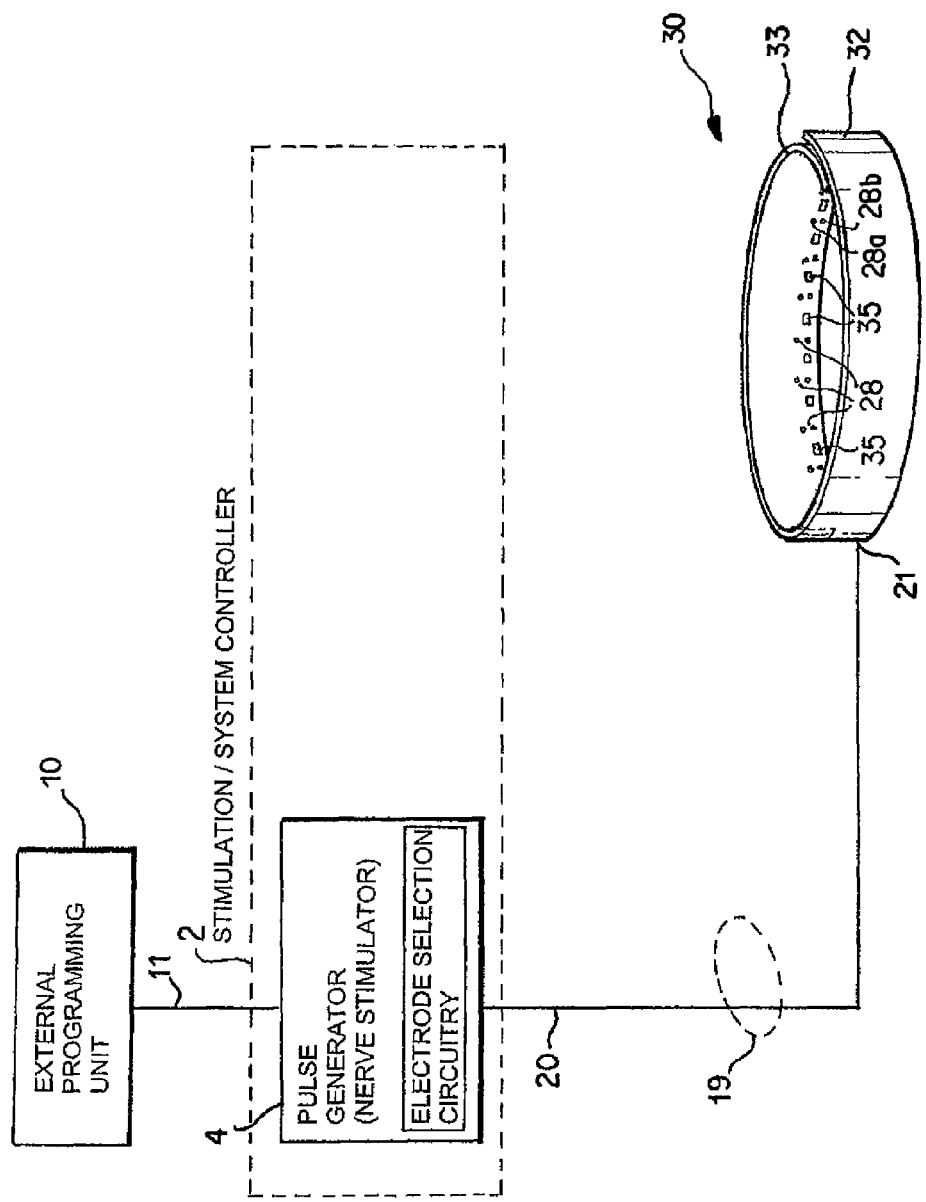
FIG. 2 is a block diagram of an embodiment of a treatment system of the present invention comprising an external programming unit, an implantable gastric band having a plurality of stimulation and sensing electrodes, an implantable stimulation controller comprising a pulse generator, and one or more electrical leads coupling the pulse generator to the electrodes.

Although one or more of the electrical, mechanical, and chemical modes of modulation of the vagus nerve may be omitted, it is preferred that systems of the present invention comprise at least electrical stimulation via pulse generator 4, which comprises an electrical stimulation controller. An embodiment of the present invention providing only electrical modulation of the vagus nerve is shown in FIG. 2. Pulse generator 4 comprises an electronics package for generating an electrical output signal, preferably in the form of a sequence of pulses, with parameter values programmable within predetermined ranges for treating a patient having an eating disorder. A lead 20 is coupled at a proximal end to the generator 4 and at a distal end to connector 21, and delivers a programmed stimulating signal to the patient's vagus/gastric nerve(s) via stimulation electrode(s) 36. The pulse generator is preferably also capable of receiving a signal indicative of sensed or detected nerve voltage transients from sensing electrodes 28 on band 30, and to process that signal according to suitable sensing and therapy algorithms stored in a memory. The therapy algorithm is programmed by the clinician who sets the stimulation parameters of pulse generator 4.

A pulse generator suitable for use in the invention is available from Cyberonics, Inc., Houston, Tex., as the Model 102 generator. Referring again to FIGS. 1 and 2, inner surface 33 of band 30 comprises at least one, and preferably a plurality, of stimulating electrode(s) 36 for electrical stimulation of a vagus nerve or nerve branch (gastric nerve) on an exterior surface of the esophagus or stomach. As shown in FIGS. 1 and 2, electrodes 36 preferably comprise a plurality of electrode pairs 36a, 36b, which function as cathode and anode, respectively, in delivering the electrical stimulation signal to the vagus nerve(s) of the patient. Stimulation electrodes 36 may be embedded in body 32 (FIG. 1) of band 30 or, more preferably, may be coupled to inner surface 33 thereof. In certain embodiments, only stimulation electrodes 36 may be provided. In other embodiments, one or more sensing electrodes 28 may also be provided on inner surface 33. As with stimulation electrodes 36, sensing electrodes 28 preferably comprise a plurality of electrode pairs 28a, 28b.

Stimulation electrodes 36 preferably deliver electrical stimulation to a nerve structure such as the vagus nerve, and sensing electrodes 28 may sense voltage activity fluctuations on a nerve (e.g., action potentials traveling afferently and/or efferently) in response to a stimulus such as an electrical pulse from electrodes 36. Stimulating electrodes 36 allow a train of electrical pulses to be delivered to tissue (preferably nerve tissue) in electrical contact with the electrodes. Stimulation is provided according to programmed parameters of, e.g., pulse width, current magnitude, frequency, and duty cycle or on/off time. Additional details of stimulation parameters are disclosed in U.S. Pat. Nos. 5,188,104, 5,263,480, 6,587,719, 6,609,025, all hereby incorporated by reference. Sensing electrodes send an electrical signal representative of the response to the pulse generator 4, as will be further described below.

When electrodes 28 are placed immediately adjacent stimulation electrodes 36, there is a risk that electrical charge migration or leakage from stimulation electrodes 36 will result in sensing electrodes 28 detecting the stimulation signal itself, rather than the action potentials induced on the vagus nerve by the signal. To minimize this risk, it is preferred that sensing electrodes 28 and stimulating electrodes 36 be located near the ends of the upper (superior) and lower (inferior) edges of band 36, respectively. It is preferred that sensing electrodes 28 be located nearer to on the upper edge of band 30. Locating sensing electrodes 28 above the stimulating electrodes 36 serves both to minimize the strength of any current leakage from stimulating electrodes 36, and also facilitates detection of afferent action potentials on the vagus nerve induced by the stimulating electrodes 36.

As depicted in FIG. 2, band 30 preferably comprises a lead connector 21 for electrically coupling leads 20 with to the stimulating electrodes 36 and/or nerve sensing electrodes 28. Preferably, an independent electrical path is provided to each of the stimulus electrodes 36 and sensing electrodes 28, for example by a multiaxial cable or a separate wire for each electrode. Internal electrode selection circuitry in pulse generator 4 may be provided to permit each electrode 36, 28 to be independently selected for stimulation by pulse generator 4. In an alternate embodiment, the selection circuitry may be provided in band 30, allowing a reduction in the number of electrical paths that must be provided by leads 20. However implemented, the circuitry preferably allows any of stimulating electrodes 36 to be independently selected for stimulation, and any of sensing electrodes 28 to be independently selected for sensing. In one embodiment, the circuitry comprises a multiplexer and one or more address registers (not shown) to allow pulse generator 4 to select particular electrode(s) 36, 28 from among the plurality of electrodes for stimulating or sensing, respectively. Each electrode 36, 28 may alternatively be coupled to a separate lead connector (e.g., connector 21A, 21B . . . , 21$i$, not shown) and lead (e.g., 20A, 20B, . . . , 20$i$, not shown). Techniques to allow selection of specific electrodes and/or sensors from among a plurality of stimulation and/or sensing electrodes are known in the art.

Figure 3:
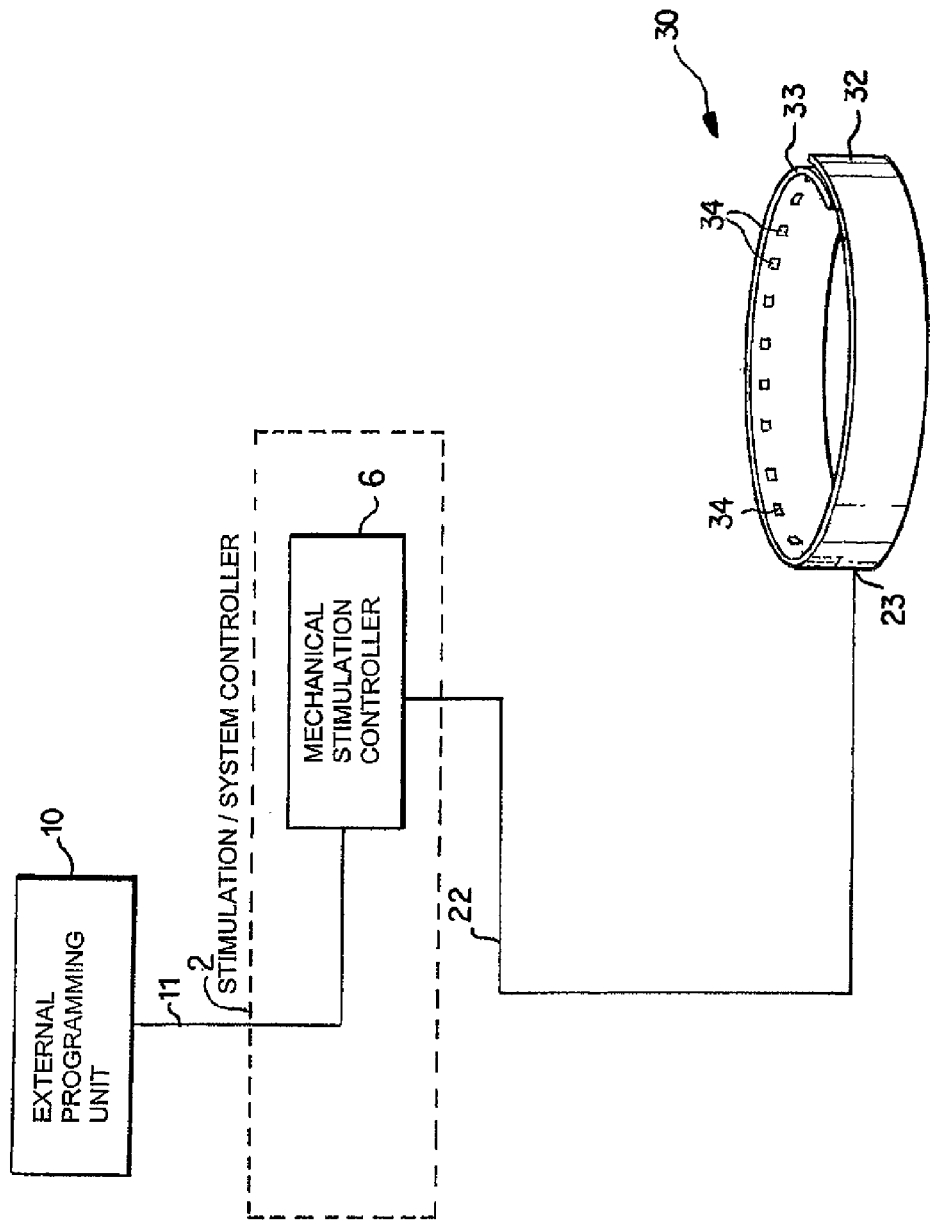
FIG. 3 is a block diagram of an embodiment of a treatment system of the present invention comprising an external programming unit, an implantable gastric band having a plurality of mechanical stimulation elements and sensing electrodes, an implantable stimulation controller comprising a pulse generator, and one or more electrical leads coupling the pulse generator to the electrodes.

Referring to FIGS. 1 and 3, mechanical stimulation of the vagus nerve is provided by mechanical stimulation controller 6 (also referred to as pressure controller 6). Band 30 may also comprise one or more mechanical stimulation elements 34 on the inner surface 33 of body 32 of band 30. A connector 23 is provided on band 30 for electrically coupling leads 22 and mechanical stimulation elements 34, which may comprise a piezoelectric vibrator element embedded in body 32 (FIG. 1) of band 30, a pressure transducer, or a displacement transducer, although a piezoelectric vibrator element is preferred. The vibrator element may deliver mechanical stimulation to a vagus nerve by vibrating in a pulsatile manner at a controlled frequency, energy amount delivered per unit time (pulse amplitude), and on/off time (pulse period). Mechanical stimulation elements 34, whether comprising a vibrator element or a different type of stimulation element, apply mechanical pressure to the vagus nerve at a desired frequency in response to a signal from pressure controller 6. Like electrical stimulation, previously described, mechanical stimulation may be used to generate action potentials on the vagus nerve, the afferent components of which travel to the brain to treat the patient's eating disorder.

Referring again to FIG. 3, leads 22 preferably provide an independent electrical path to each of the mechanical stimulation elements 34, either by a multiaxial cable or a separate wire for each element. Additionally, mechanical stimulation controller 6 also preferably includes selection circuitry to allow the controller 6 to individually select desired stimulation element(s) 34 from among a plurality of such elements for modulation of the vagus nerve. Techniques, such as multiplexing and registers storing addressable stimulation leads that allow for the selection of specific elements from among a plurality of elements, are known in the art. In less preferred embodiments, the selection circuitry may be provided in band 30, and mechanical stimulation elements 34 may all be addressed and energized simultaneously.

Figure 4:
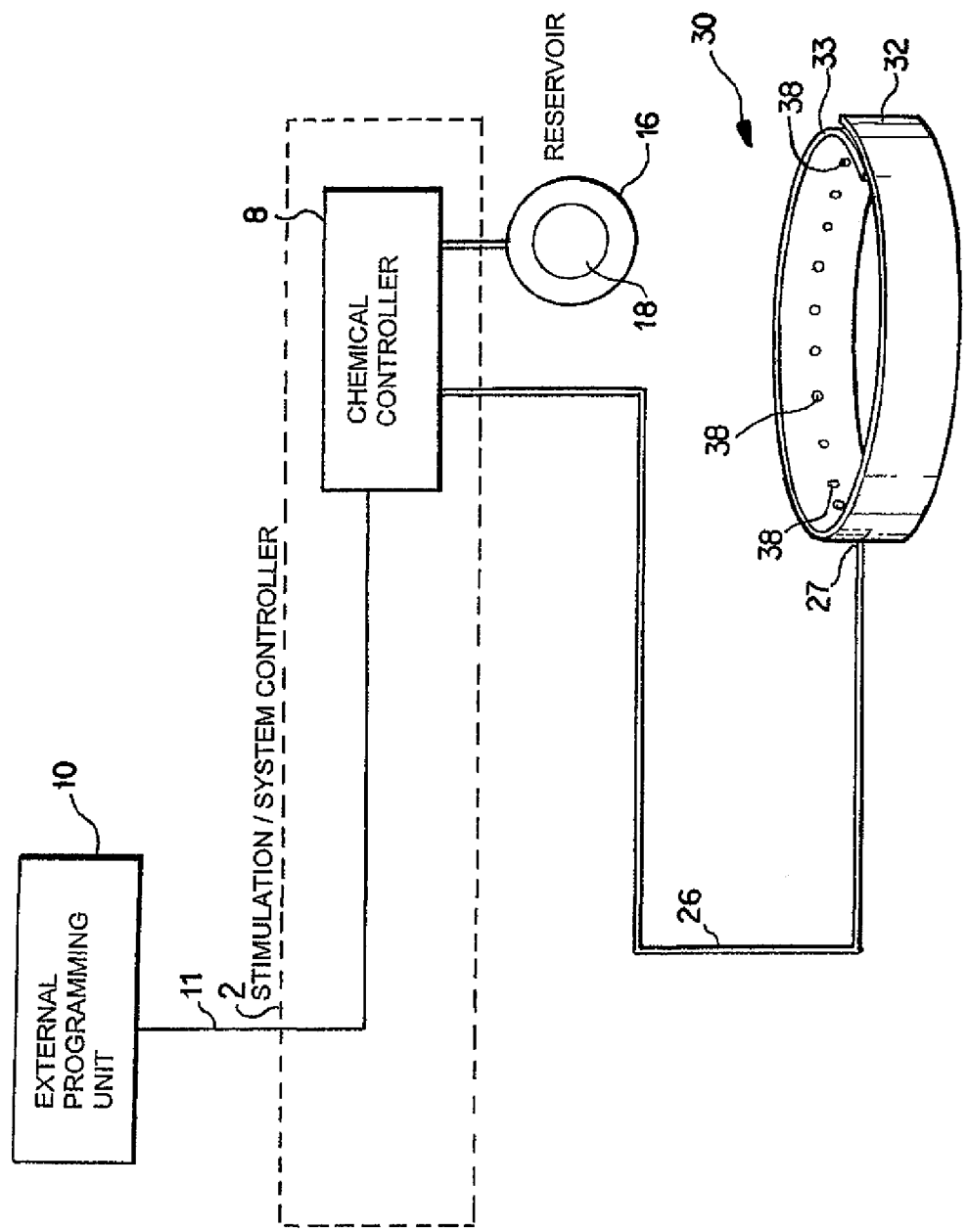
FIG. 4 is a block diagram of an embodiment of a treatment system of the present invention comprising an external programming unit, an implantable gastric band having a plurality of chemical outlet ports, an implantable chemical controller comprising a pump, a reservoir for storing a chemical agent, and tubing lines coupling the reservoir to the chemical controller and coupling the controller to the outlet ports. An access port in the reservoir may be provided to allow additional agent to be delivered to the reservoir.

In a third mode of providing neurostimulation, embodiments of the present invention may also provide chemical stimulation to suppress appetite. Referring to FIG. 4, a chemical controller 8, in conjunction with chemical reservoir 16, may provide chemical stimulation of the vagus nerve. In this embodiment, band 30 is provided with one or more chemical outlet ports 38 on body 32. Controller 8, which preferably comprises a pump, delivers a chemical stimulation agent from reservoir 16 to outlet ports 38. Each outlet port 38 may comprise a valve or pierceable seal (not shown) that prevents the chemical from diffusing or flowing out without operation of the pump or other flow delivery means (e.g., a syringe). A chemical inlet line 26 provides communication between chemical controller 8 and band 30 via a connector 25, which is in turn in communication with chemical outlet ports 38. Reservoir 16 is coupled to controller 8 by a conduit or tube 17, and may comprise an implantable reservoir that may be refilled by percutaneous injection via an access port 18. Alternatively, access port 18 may permit delivery of a removable catheter reservoir containing the agent. Such a reservoir may be periodically delivered, used, removed, and replaced by a fresh catheter. Suitable pumping or controlled release devices which may be adapted for use in chemical controller 8 are disclosed in U.S. Pat. Nos. 6,571,125 and 6,356,784, both assigned to Medtronic, Inc. Chemical controller 8 may include a receiver for receiving and processing a transcutaneous electromagnetic signal (e.g., RF signal) and a signal converter for directly causing a pump to move the agent from reservoir 16 to outlet(s) 38 in response to an externally applied electromagnetic signal.

In an alternative embodiment, chemical controller 8, reservoir 16, access port 18, and outlet ports 38 may be omitted and instead the body 32 of band 30 may comprise, or be coated with, a chemical-eluting material such as a polymer matrix (not shown) containing a chemical agent, such as a drug or antibiotic, for treating a particular patient, preferably by stimulating a vagus nerve. For instance, the chemical/matrix coating may be made to elute the chemical agent over a desired period of time after implantation. Known degradation rates of various degradable polymers may be used to provide a polymer matrix having a desired elution profile for a particular chemical agent. Polymer matrices suitable for use in delivering one or more chemical agents may comprise one or more biodegradable polymers such as polylactic acids, polyglycolic acids and other polyhydroxy acids, polycaprolactone, and other slowly degrading polymers, or may comprise biostable polymers such as polyurethanes, silicones, acrylates, polyesters, polyethylene oxides, polyalcohols, and polyolefins, by way of nonlimiting example. Other biodegradable and biostable matrix materials are well-known in the art, and it will be appreciated that any suitable controlled-release chemical-eluting material could be substituted. More generally, the placement of electrodes, sensors, pressure applicators, chemical outlets and connectors may be varied, and the appearance of the gastric band may differ from those shown in FIGS. 1-4 without negatively affecting the operation of the assembly.

In addition to providing nerve stimulation capability, gastric band systems of the present invention also preferably provide the capability of post-operatively and non-invasively adjusting the circumference of band 30 around the esophagus/stomach, thereby altering the degree of constriction that band 30 provides to the patient's gastric system. In current gastric band systems, the physician typically adjusts the constriction of the band during surgery by inflating one or more expansion members with a hydraulic fluid to provide a fixed degree of constriction, which can only be changed with further surgical intervention or invasively by percutaneously inserting a needle into an implanted reservoir to add or withdraw hydraulic fluid from the band. In either of the current ways of post-operatively adjusting the band, the patient is subjected to a painful and potentially dangerous process. In systems of the present invention, by contrast, post-operative changes in constriction can be made non-invasively whenever desired by commands from an external programming unit.

Figure 5:
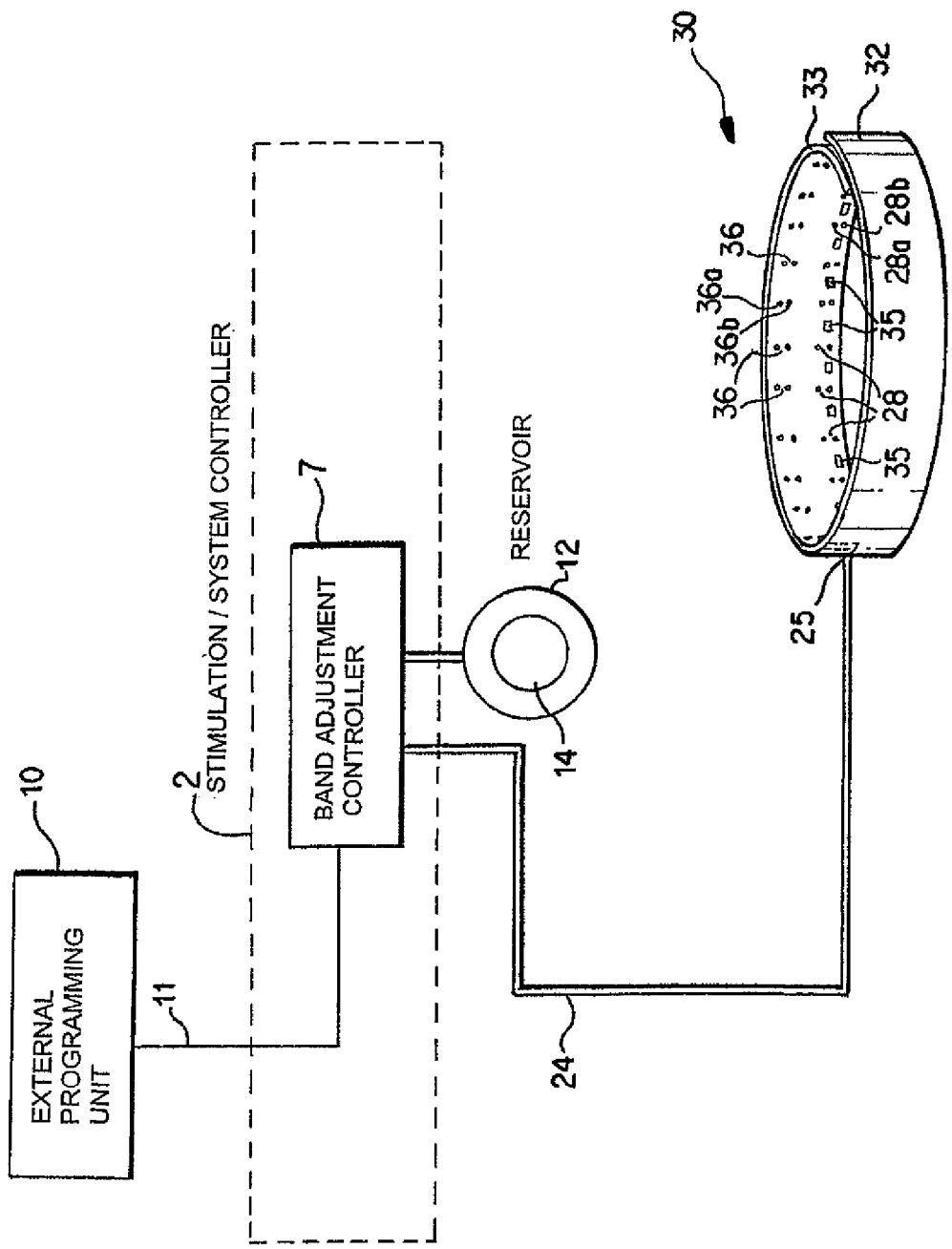
FIG. 5 is a block diagram of an embodiment of a treatment system of the present invention comprising a band adjustment controller for allowing non-invasive, post-operative adjustments to be made to the band to change the degree of restriction provided to the esophagus/stomach.

An embodiment of a post-operatively adjustable gastric band is shown in FIG. 5. In general, a band adjustment controller 7 may be used to control a constriction adjustment element coupled to band 30. The band adjustment controller may be actuated or programmed by external programming system 10, allowing post-operative, in situ adjustments to the band's constriction upon the patient's gastrointestinal tract. The constriction adjustment element increases or decreases the level of constriction of the gastrointestinal tract under the control of the band adjustment controller, facilitating therapy regimes previously impossible in prior art gastric bands. In one embodiment, the constriction adjustment element comprises one or more expansion members that may be inflated or deflated by adding or removing a hydraulic fluid from the expansion members. In other embodiments, the adjustment element comprises a mechanical adjustment system such as a radiator clamp-type belt and a screw or worm gear adjustment, a rack-and-pinion adjustment system, or other mechanical devices for adjusting a circumferential member.

Referring to FIG. 5, the system is provided with a reservoir 12 containing a hydraulic fluid, such as mineral oil, saline or other biologically compatible fluid. Reservoir 12 may also include a sensor (not shown) to indicate when the reservoir is low or empty. A fluid reservoir access port 14 may optionally be provided to allow hydraulic fluid to be added to or removed from the system after the system is implanted. The access port preferably comprises a self-sealing membrane into which a needle may be inserted transcutaneously to add or withdraw fluid from the reservoir 12. The fluid may be delivered by band adjustment controller 7 from reservoir 12, via fluid line 24, to inflate one or more expansion members (not shown) incorporated in band 30. The expansion members may be located within body 32, or coupled to a surface of band 30. In one embodiment, one or more hollow chambers are provided in body 32 to function as the expansion member. In another embodiment, one or more balloon members may be coupled to inner surface 33 of band 30. By inflating the expansion members, the degree of constriction of the esophagus/stomach is increased. Constriction may be reduced by removing the hydraulic fluid from the expansion members and returning it to reservoir 12. A connector 27 couples fluid line 24 to band 30 and the expansion members. Band adjustment controller 7 may include a receiver for a transcutaneous electromagnetic signal (e.g., RF signal) and control logic or circuitry implementing a treatment algorithm for directly causing a fluid pressure change in band 30 in response to an externally applied electromagnetic signal.

Referring to FIG. 5, it is desirable that the treatment system also include the ability to determine and report to an external user an indication of how much restriction has been provided by the adjustment element. The band adjustment controller 7 preferably provides a constriction indication signal, which allows a healthcare provider to precisely adjust or alter the therapy provided to the patient. The constriction indication signal may be transmitted wirelessly to external programmer 10 upon inquiry, and the external programmer 10 preferably provides a graphical or other visual indication of the degree of constriction to the healthcare provider. In a preferred embodiment, band adjustment controller 7 comprises a reversible pump (not shown) capable of pumping fluid either from the reservoir to the expansion members or from the expansion members back to the reservoir. In this embodiment, a constriction indication may be provided by calibration circuitry in the band adjustment controller. The calibration circuitry is coupled to the reversible pump to indicate how much fluid has been pumped into the expansion members at any given point in time. In one embodiment the reading may comprise a numerical percentage indication, from 0% to 100%, of how much fluid relative to its maximum capacity has been added to the expansion members.

In another embodiment, the constriction indication signal may be provided by incorporating one or more pressure sensors 35 on band 30 to sense the degree of constriction provided by the band. As the band tightens around the esophagus/stomach, the increased pressure sensed by the pressure sensors provides a signal that corresponds to the increased constriction. Calibration circuitry in the band adjustment controller uses the electrical signals from the pressure sensors to provide a constriction indication signal, which may correspond to a numerical designation from 0-10 to indicate the relative degree of constriction, with zero indicating no constriction and ten indicating a maximum constriction setting consistent with patient safety. The pressure sensors 35 may comprise electrodes positioned on the inside surface 33 of band 30, and may be coupled to band adjustment controller 7 by a lead (not shown) similar to lead 20 for pulse generator 4 as shown in FIG. 1. The pressure signal from sensors 35 may then be used as a constriction indication signal directly by band adjustment controller 7, which may comprise a treatment algorithm in which the constriction is altered according to a predetermined schedule. Alternatively, the signal may be transmitted to the external programmer 10 and the constriction displayed to the healthcare provided, who may then add or withdraw fluid to or from the expansion member(s) of band 30 and thereby change the degree of esophagus/stomach constriction as desired. The pressure sensors may alternatively comprise a fluid pressure sensor (not shown) within the expansion members. It will be appreciated, however, that any suitable pressure sensing device known may be incorporated into band 30 and used with calibration circuitry to provide a constriction indication.

In a further embodiment, pressure sensors 35 may be used to provide a relatively constant pressure on the esophagus/stomach. One or more of sensors 35 may provide pressure indications at a desired sampling rate (e.g., once per second, once per minute, twice per hour, once per day or longer). The time series pressure signals may be used by adjustment controller 7 in a treatment algorithm to add or withdraw fluid from the expansion members so as to maintain a relatively constant pressure (as opposed to a constant degree of restriction) on the esophagus/stomach. The treatment algorithm may comprise a program executed by control logic. This embodiment provides the advantage of allowing the esophagus/stomach to maintain some degree of its natural motility, while also providing restriction to prevent the patient from overeating. Such modes of treatment are not available in current devices.

Although mechanical stimulation of the vagus and/or gastric nerves and branches thereof is preferably accomplished with vibrator elements, low-frequency stimulation of the vagus nerve may also be provided by using band adjustment controller 7, reservoir 12 and tube 24 to provide one or a series of fluid pulses of defined frequency, intensity and duration, causing the band or inflatable member to take in fluid, inflate or enlarge, and cause constriction or pressure on vagus nerves underlying the tissue contacted by band 30 or an inflated portion thereof, and then withdraw the fluid to relieve the pressure. This is preferably accomplished during an initial adjustment procedure, similar to those described previously, in which the healthcare provide notes any nausea, retching, "fullness" sensations, or other indicators associated with certain fluid pulse parameters. When the fluid pulse characteristic(s) that produce(s) a selected level of response in the patient (e.g., fullness, nausea, retching) are identified, a fluid pulse threshold is thus obtained, and the clinician would then adjust the programming of the band adjustment controller 7 to only administer fluid mediated stimuli that are below that threshold level.

External programming unit 10 is used to control the operation of each type of modulation controller 4, 5, and 6, as well as band adjustment controller 7. External programming unit 10, shown in simplified block diagrammatic form in FIG. 1, comprises electronic circuitry, typically including a processor, programmable memory, and a display or other data output device (not shown). The external programming unit 10 also comprises software that may be used to program system controller 2, and more specifically pulse generator 4, mechanical stimulation controller 5, chemical stimulation controller 8, and band adjustment controller 7, with sensing, analytic, therapy, and/or constriction algorithms appropriate for the particular treatment regimen desired. System controller 2 preferably comprises a programmable communications interface coupled to one or more of sub-unit controllers 4, 5, 6, and 7. After implantation of system controller 2, band 30, and the associated connecting leads and conduits for each respective modulation/adjustment system included in the overall system 1, the external programming unit 10 is preferably capable of wireless communication with the modulation/adjustment controllers 4, 5, 6, and/or 7 for conducting monitoring, diagnostic and programming functions.

Programming unit 10 is also preferably structured to provide user interface functions, e.g., straightforward, menu-driven operation, "help" functions, prompts, and messages to facilitate simple and rapid programming and programming modifications, and displaying or reporting desired data and events relating to the stimulation/adjustment controllers 4, 6, 8 and 7. The programming capabilities preferably allow modification of the programming of the stimulation/adjustment units to set or change adjustable parameters and to test device diagnostics. External programming system 10 is preferably also capable of receiving signals from the stimulation units corresponding to data such as parameter settings on the respective stimulation units 4, 6 or 8, or the current restriction status/setting for band 30.

The external programming unit 10 may be used to program the system controller 2 to operate any one of the stimulation modalities alone, or any combination of those modalities, either independently or in concert. Thus, a useful treatment system may omit one or two of the three modalities. For instance, the capability for chemical stimulation of the vagus nerve may be eliminated by omission of chemical controller 6, reservoir 16, tube 26, connector 27, and outlets 38 (and any chemical eluting matrix). Similarly, the capability for mechanical stimulation may be eliminated by omission of mechanical modulation controller 5, reservoir 12, lead 22, connector 23, and mechanical modulation elements 34. Another alternative configuration could omit the electrical pulse generator 4, lead 20, connector 21, and stimulation and sensing electrodes 36, 28 if electrical stimulation or nerve sensing will not be employed.

Other capabilities of the programming and electronic circuitry of external programming unit 10 and various components of control system 2 may include the capability to store and retrieve historical data. For example, patient code, device serial number, number of hours of battery operation, number of hours of stimulation output, and number of manual activations (indicating patient intercession) for display on a screen with information showing date and time of the last one or more activations.

The overall treatment system, which preferably includes implantable components and external programming components, is preferably noninvasively calibrated for a particular patient by telemetry from the external programming unit 10. The implanted electronics package may be externally programmed for activation upon occurrence of a predetermined detectable event (such as nerve activity detected by sensors 28), or may be periodically or continuously activated according to a programmed duty cycle, to generate the desired stimulation signal, which is applied to the patient's anterior and/or posterior vagus nerves, or branches thereof, to modulate vagal activity to treat an eating disorder, e.g., treating obesity by reducing appetite or producing a feeling of satiety.

External programming unit 10 is preferably capable of wireless communication with any of the sub-unit controllers 4, 5, 6 and 7, as designated by line 11 in FIG. 1. Details for such communication are known in the art. More specifically, external programming system 10 is capable of communicating transcutaneously with at least pulse generator 4 of system controller 2 via transmission and reception of electromagnetic signals (e.g., radiofrequency signals (RF)). Alternatively, a percutaneous lead (not shown), may be used as communication path 11. However, wireless communication minimizes the risk of potential infection by avoiding a path from outside the body to the abdominal cavity along the lead.

Positioning and Adjusting the Treatment Assembly.

Figure 6:
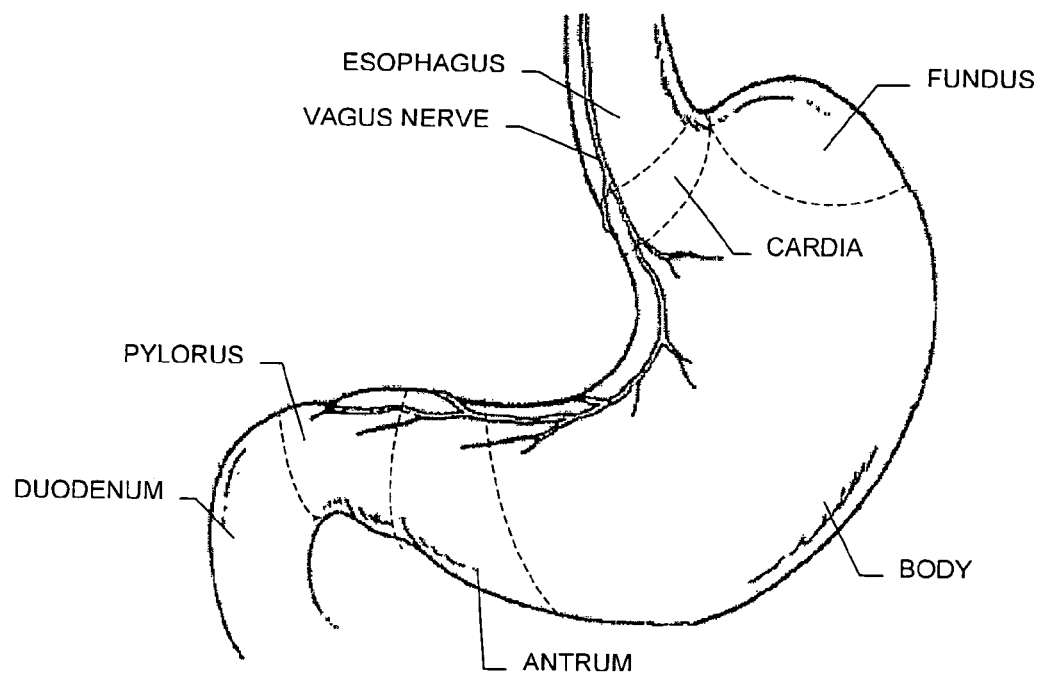
FIG. 6 is a simplified partial front view of the human stomach showing the cardia, fundus, body, antrum and pylorus regions and showing typical branching of the left vagus nerve on the anterior surface of the stomach.
Figure 7:
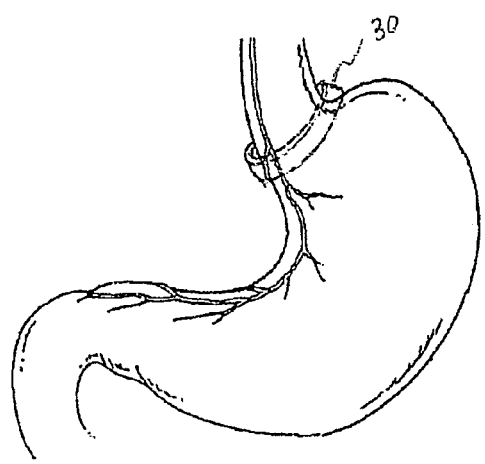
FIGS. 7, 8 and 9 are simplified front views of the human stomach illustrating three exemplary placement locations for gastric bands that include stimulation elements and sensors, in accordance with representative embodiments of the present invention.
Figure 8:
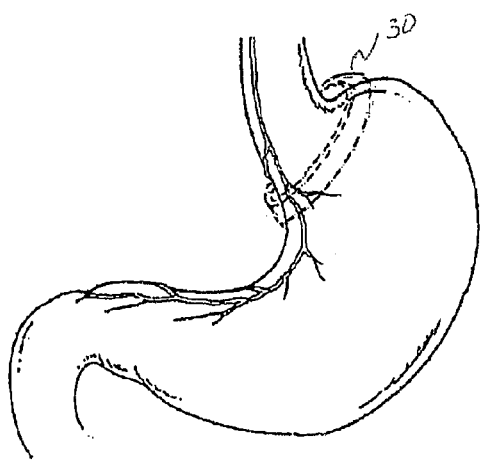
Figure 9:
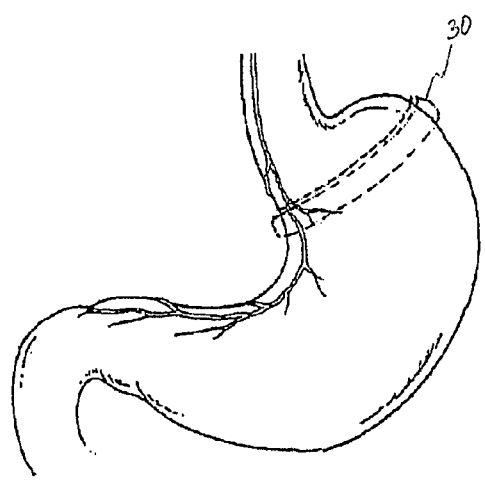

FIG. 6 illustrates in a simplified manner the lower esophagus and the cardia, fundus, body, antrum, pylorus and duodenum regions of the human stomach, and the primary vagal/gastric nerve branches along the anterior surface of the stomach. FIGS. 7, 8 and 9 are simplified front views of the stomach showing a range of representative placement locations for gastric bands with vagus nerve modulation capability. Electronic components are not shown in FIGS. 7-9 to enhance the clarity of the placement locations depicted. In FIG. 7, the band encircles the lower esophagus/upper cardia. In FIG. 8 the band encircles the central cardia region. In FIG. 9 the band spans the lower cardia and fundus regions, and encompasses the uppermost portion of the body of the stomach.

The exact placement of the band may vary from the positions shown in FIGS. 7-9, in accordance with the healthcare provider's judgment with respect to the particular patient being treated. In embodiments involving neuromodulation, at least one stimulation controller must be included to provide a stimulation signal or agent to band 30 in operational relation to at least one vagus nerve or gastric vagal branch, i.e., in a manner that is effective for reducing the patient's appetite or inducing a feeling of satiety when assembly 1 is operated to stimulate the nerve or nerve branch. For optimally sensing a nerve response, and/or for optimally applying electrical pulses to a nerve, one or more nerve sensing electrodes 28 or stimulating electrodes 36 on band 30 is preferably positioned directly over a vagal/gastric nerve or nerve branch.

Systems of the present invention may be implanted by a number of surgical procedures, such as open or closed laparotomy or thoracotomy. Minimally invasive procedures are preferred to facilitate patient recovery and to minimize scar tissue formation. During the same surgical procedure in which band 30 is coupled to the patient's esophagus/stomach region, controller 2 (depicted in FIGS. 1-5) is also implanted in the patient's body, preferably in the abdominal region below the diaphragm; for example, via a left laparotomy incision. Lead 20 (electrical modulation), lead 22 (mechanical modulation), tubes 17 and 26 and chemical reservoir 16 (chemical modulation), and tubes 15 and 24, and pressure fluid reservoir 12 (band adjustment) are also implanted during the procedure. The leads and tubes are connected as shown in FIGS. 1-5. The fluid reservoir access port 14 is preferably placed below the skin below the rib cage to allow for fluid to be injected, e.g., by a needle percutaneously inserted into reservoir 12 via port 14. Similarly, the chemical access port 18 may be located below the skin below the rib cage to allow for ease of filling or emptying of the reservoir 16 via port 18.

Reservoirs 12 and 16 are preferably filled in advance of surgery, with the desired pressure fluid or chemical solution, respectively, and may also be filled (or refilled) in situ via ports 14 and 18 after implantation of the reservoirs. Alternatively, in instances in which one or both of chemical controller 6 and band adjustment controller 7 are omitted from system controller 2, application of a chemical agent (e.g., an antibiotic) via outlet(s) 38 and/or inflation of expansion members coupled to band 30 may be manually effected, respectively, by injecting or withdrawing chemical solution or hydraulic fluid via ports 14 and/or 18.

Programming methods known in the art for neurostimulators may be used to program system controllers 2 and/or sub-controllers 4, 5, 6, and 7. For embodiments employing electrical modulation, pulse generator 4 may be programmed by a healthcare provider, preferably by telemetry (e.g., using an RF programming wand) in communication with external programming unit 10. The healthcare provider may also run one or more diagnostic procedures on pulse generator 4, and/or receive data from the generator.

An initialization program, which may be stored either in the external communication unit 10 or in the pulse generator 4, is preferably executed at the time the implant is first programmed after implantation. The initialization program is used to determine which stimulating electrodes 36 and which sensing electrodes 28 are nearest one or both of the anterior and posterior vagus nerves. Electrical stimulation and sensing of the vagus nerve requires that the electrodes be either in direct contact with the vagus nerve or are in close proximity thereto. Accordingly, in preferred embodiments only the stimulating electrode(s) 36 and sensing electrode(s) 28 that are nearest the vagus nerve are used to stimulate and sense the nerve, since energizing all of the stimulating and sensing electrodes simply depletes the battery of the pulse generator 4 with no corresponding benefit to the patient.

A number of initialization processes may be used to determine the electrodes 36, 28 nearest to the anterior and/or posterior vagus nerves. Algorithms for the initialization processes are preferably maintained in a memory, and executed by an initialization controller, in pulse generator 4. In whatever procedure is used, the surgeon must first secure band 30 to the esophagus/stomach. After the band is attached to the GI tract it is unknown, prior to initialization, which sensing and stimulating electrodes are located nearest to the vagus nerve(s) and thus are the best electrodes for delivering the electrical stimulation to the nerve. However, by sequentially energizing one or more stimulating and sensing electrodes, it is possible to determine which stimulating and sensing electrodes are located nearest the anterior and/or posterior vagi.

In one initialization process, all of the stimulating electrodes 36 are simultaneously energized in a series of pulses, and individual sensing electrodes are sequentially used during and/or immediately after each of the stimulation pulses in an attempt to detect an action potential on the vagus nerve induced by the stimulating electrodes. The parameters used for the initialization stimulating pulses are set so as to reliably generate an action potential on the nerve, i.e., the pulses have a relatively high amplitude such as 6 microamperes, and have a relatively long pulse width such as 1.0 milliseconds. The timing sequence for energizing the sensing electrode(s) relative to the stimulation electrodes may be varied across a wide spectrum with acceptable results. In one embodiment, the sensing electrodes may be energized simultaneously with the stimulating electrodes, and for the same duration. In another embodiment, the sensing electrodes may be energized slightly after the leading edge of the stimulation pulse (e.g., with a delay of 100 microseconds) and the sensing pulse may extend for a period slightly beyond the stimulating pulse to ensure that any action potentials generated near the end of the stimulation pulse are sensed.

In a preferred embodiment, for each of the stimulation pulses energizing all of the stimulation electrodes, one (and only one) of the sensing electrodes 28 (which preferably comprises an electrode pair adapted to sense activity at a particular location on the inner surface 33 of the band 30) is correspondingly energized to determine whether or not the stimulation pulse produced a voltage transient indicative of an induced action potential. If such a voltage transient is detected, the address of the sensing electrode and the magnitude of the action potential measured are noted. After the first stimulation and sensing pulses, a second stimulation pulse is made, and a second sensing electrode is used to sense any voltage transients corresponding to induced action potentials. As with the first pulse, if a voltage transient is detected, the address of the sensing electrode and the magnitude of the action potential measured are noted. Additional stimulating and sensing steps are performed until all of the sensing electrodes have been used, with any detected voltage transients recorded along with the address of the sensing electrodes.

After all of the sensing electrodes have been used to detect induced action potentials, the electrodes detecting the largest magnitude pulses are determined by comparing the detected voltage magnitudes. The electrodes having the highest detected voltage magnitudes will be the electrodes nearest to the anterior and posterior vagus nerves. Depending upon the location of the electrodes relative to the vagus nerves, it is believed that one or two of the sensing electrodes will have significantly higher voltage magnitudes for each branch of the vagus nerve, indicating that those electrodes are closest to the vagus nerve. In preferred embodiments, once the locations of the vagus nerve branches are known, the stimulating electrodes 36 that are adjacent to the sensing electrodes nearest to the nerves are thereafter the only electrodes used for stimulation. These stimulating electrodes can be determined from the known addresses of the stimulating electrodes and their positions relative to the sensing electrodes nearest to the vagus nerves. It will be understood that, although the process has been described using only a single sensing pulse to test the response of each sensing electrode, a plurality of pulses may also be used to confirm that the electrode does (or does not) lie adjacent to a branch of the vagus nerve.

In another embodiment, individual stimulation electrodes (instead of all of the stimulation electrodes) are individually and sequentially energized with electrical pulses of sufficient magnitude to generate an action potential on the vagus nerve if the electrode is either in direct contact or closely adjacent to the nerve. Preferably, a plurality of pulses are provided to the electrode to allow the detection (or non-detection) of the action potential to be confirmed by repeated stimulation and detection steps. In this embodiment, a single stimulation electrode delivers one or more electrical pulses, and one or more sensing electrodes are used to sense any induced action potentials. In this embodiment, it is preferred that all of the sensing electrode pairs are simultaneously used to detect an induced action potential, and the magnitude and location of any sensed voltage fluctuation is noted. Alternatively, for each individual stimulation electrode, several of the sensing electrodes near to the stimulation electrode may be used, individually and sequentially, to detect any induced action potential. This approach provides a more detailed view of which electrodes are near the vagus nerve, but may take a longer time to perform because more combinations must be tested. Regardless of whether all or only a portion of the sensing electrodes are used, the sensing step should be timed relative to the stimulation test pulse according to a timing designed to reliably detect any action potential induced by the stimulating pulse. In one embodiment, the sensing electrode is energized at the start of the stimulation pulse and the sensing pulse continues for a period of time, e.g., 100 microseconds, after the stimulation pulse has ended. In another embodiment, the stimulation pulse begins slightly after the stimulation pulse, e.g., 50 microseconds, and is discontinued at the same time as the stimulation pulse. Because the goal is simply detection of a large signal, the timing is not critical, and persons of skill in the art may readily arrive at suitable timing parameters for the stimulation and sensing pulses to enable the sensing electrode to determine whether or not the stimulating electrode has induced an action potential on the vagus nerve.

If the sensing and stimulating electrodes are adjacent to one of the branches of the vagus nerve, the sensing electrode will detect a voltage transient associated with an action potential generated by the stimulation electrode. If one or both of the stimulating and sensing electrodes are not in contact with or adjacent to the vagus nerve, no transient will be detected. In either case, the magnitude of the voltage across the sensing electrode is recorded.

Subsequent stimulation therapy may then use only those stimulation electrodes identified in the initialization process as closest to the vagus nerve, avoiding unnecessary energy expenditure associated with energizing electrodes having no effect on the vagus nerve. Thus, after determining which electrodes and sensors provide satisfactory, preferably optimal, stimuli or responses, the programming in pulse generator 4 preferably comprises additional electrode lockout software to automatically use only the stimulation and sensing electrodes identified in the initialization routine in subsequent stimulation therapy. The program may be re-executed at the direction of a healthcare provider if, for example, the band 30 moves relative to the esophagus/stomach or vagus nerve such that the stimulating and sensing electrodes 36, 28 are no longer in direct contact with (or closely adjacent to) the vagus nerve. Alternatively, software may automatically re-initialize the electrodes at a desired interval, which may range from once each day to once per month, once per year, or longer.

After the electrode initialization procedure is executed, therapeutic diagnostic procedures following the initial implant may then continue with the health care provider administering via the selected stimulation electrodes and pulse generator 4 a series of electrical pulses of known voltage, frequency, pulse width, and duty cycle. The provider notes any feelings reported by the patient of nausea, retching response, "fullness" sensation or pain associated with certain pulse parameters. For example, if the vagus nerve is stimulated excessively, in one embodiment characterized by a current amplitude that is too high, a retching response typically occurs. When the pulse characteristic(s) that produce a selected level of response in the patient (e.g., nausea, retching, satiety, pain) are identified, a pulse threshold is thus obtained, and the health care provider would then adjust the programming of the pulse generator 4 to only administer stimuli that are below that threshold level. For example, if the therapeutic level of pulse current is programmed to a value less than approximately 6 mA, a typical patient will not experience retching attributable to vagus nerve stimulation, although variations in response may occur from one patient to another. See, e.g., U.S. Pat. Nos. 6,609,025 and 6,587,719. In any event, the maximum amplitude of the current is preferably adjusted accordingly during the initial diagnostic procedure until an absence of retching is observed, and a suitable current amplitude safety margin is programmed into the pulse generator.

The retching threshold may change noticeably with time over a course of several days after the pulse generator begins delivering therapy to the patient. Accordingly, the therapeutic diagnostic test is preferably checked again after implantation, especially during the first few days after implantation to determine whether any adjustment is necessary to maintain an effective therapeutic regimen. Preferably any adjustments in programming that are necessary after the implantation procedure and initial setup are made via telemetry. Carrying out the above-described customized therapeutic and electrode initialization diagnostics are preferred because some differences can be expected from one pulse generator to another due to idiosyncratic variables in each treatment situation. For example, differences in the optimum current magnitude of current in the stimulation signal pulses may be observed from one patient to another, which may be attributable to such factors as patient impedance, anatomical variation in vagus nerve location and branching between patients, and variations in electrode/tissue contact from one implant to another. Where the stimulation and sensing electrodes directly contact a vagus nerve branch, lower energy is necessary for providing effective stimulation, and battery life is correspondingly lengthened. If, on the other hand, the stimulation and sensing electrodes are located slightly off the vagus nerve, and there is no direct stimulation or sensing, the energy necessary to provide effective stimulation will be higher, and battery life will be significantly reduced.

In systems incorporating mechanical stimulation of the vagus nerve or branches thereof, proper placement of band 30 includes ensuring that one or more mechanical stimulation element 34 is positioned over or sufficiently close to a nerve or nerve branch to cause action potentials to be generated on the nerve. Determination of which mechanical stimulation elements 34 should be used may be accomplished by a procedure similar to that described for stimulation electrodes 36. Of course, this can only be done if sensing electrodes 38 are provided on band 30

Similarly, if chemical stimulation of the target nerve(s) is incorporated into the system, one or more chemical outlet 38 on band 30 is operably situated, preferably over, or in close proximity to, a target nerve or nerve branch. For instance, a number of spaced apart chemical outlets 38 may be arrayed along the inner surface of band 30, however each comprises a removable closure or pierceable seal that prevents the chemical from diffusing out. Identification of which chemical outlets 38 are nearest to the vagus nerve may not be possible by processes similar to those described for identifying which electrodes are nearest to the vagus nerve, because diffusion of the agent from the chemical outlets 38 to the vagus nerve cannot be reliably correlated by sensing electrodes to distance from the nerve. Accordingly, locating the outlets 38 near the vagus nerve may be best accomplished by provided visual or other indications for the surgeon to ensure that one or more ports can be located generally near the anterior and posterior vagus nerve branches, as opposed to a sensing-and-verification process.

Systems of the present invention may also include diagnostics testing algorithms to verify proper operation of the device, and to indicate the existence of problems such as with communication, batteries, or lead/electrode impedance. A low battery reading, for example, would be indicative of imminent end of life of the battery and need for replacement. When an implanted component is interrogated during or after initial setup of the treatment assembly, the then-present state of the adjustable parameters is preferably displayed by the external programming unit 10 so that the healthcare provider may conveniently review and change any or all of those parameters, as appropriate. Preferably, if a particular parameter is selected for change, all permissible values for that parameter are displayed so that the healthcare provider may select an appropriate desired value for reprogramming the stimulus generator.

Systems of the present invention also provide the capability for completely new therapies not previously available in prior art gastric bands. In particular, because the restriction to the esophagus/stomach provided by the band may be continuously and noninvasively adjusted, the band adjustment controller 7 may be programmed to increase the gastric restriction of band 30 at selected times during the day and decrease it at other times. In one embodiment, systems of the present invention may be programmed to increase the level of constriction according to the circadian cycle of the patient, such as at mealtimes, and to decrease the level of constriction at other times such as between mealtimes and during sleep periods. In another embodiment, the system may be programmed to provide a pulsating restriction oscillating between a first and a second pressure (or degree of restriction) during most of the day, and to provide a constant third pressure (or degree of restriction) greater than the first and second pressures at mealtimes. In still further embodiments, the gastric band may provide another restriction regime during sleep.

The patient may also be provided with a manual activation means (e.g., a magnet placed over the band adjustment controller 7, or a sensor system controller 2 responsive to taps on the skin overlying system controller) to increase or decrease the constriction provided by band 30. Inflation or expansion to increase constriction may be mechanically controlled either electromechanically (e.g., by moving a piston radially inward or outward on band 30) or electrohydraulically (e.g., by increasing or decreasing saline pressure in one or more inflation member in band 30). As mentioned above with respect to the apparatus description, band adjustment controller 7 preferably includes programmed instructions and/or components for receiving appropriate externally applied programming or instructions.

Therapeutic Use of the Treatment Assembly

A severe limitation of existing gastric bands is the pain associated with the patient adjusting to a new, substantially lower, food intake level. The present invention assists the patient in this process by removing or substantially lessening such pain. Without being bound by theory, it is believed that slowed eating and lack of enthusiasm in food consumption arising from VNS is centrally mediated, and that the result of therapeutic nerve stimulation is a positive response of inducing a sensation of satiety mimicking that which would occur after consumption of a full meal, rather than a negative response of nausea or sick stomach. Accordingly, the pain associated with severely reducing caloric intake is substantially eliminated, allowing substantially higher compliance with the therapy by the patient population.

The above-described systems are useful for the therapeutic treatment of an obese person to promote a reduction in food intake and facilitate weight loss. After implantation of the system into the patient's body and after adjustment of programming and/or band restriction as previously described, the vagus nerve stimulation (VNS) therapy is initiated. VNS therapy may be supplemented by constriction of the stomach to create a smaller entrance to the stomach (stoma) which will tend to limit the amount of food consumed and will tend to allow less food to pass into the stomach. The patient's eating behavior is preferably allowed to stabilize after surgery before the therapeutic nerve stimulation regimen is actually implemented. If little or no gastric constriction is employed, the patient's eating behavior may stabilize at approximately the preoperative level.

Preferably, programmed cyclic or periodic pulsatile stimulation of the nerve(s) is provided, in a circadian rhythm. For example, vagus nerve stimulation at or near the esophagus/stomach juncture is periodically administered between mealtimes during normal waking hours according to the patient's circadian cycle, to suppress the patient's appetite by producing the sensation of satiety in the patient between normal mealtimes. Stimulation may be terminated at a preset time prior to normal mealtimes, and may also be restarted during the mealtime itself (or shortly thereafter) to help the patient to avoid overeating.

An alternative VNS treatment regimen includes modulation of vagus nerve electrical activity by chronic intermittent nerve stimulation over each twenty-four hour period. The intermittent cycles of stimulation are maintained according to a programmed or preset duty cycle. The pulse signal is programmed to have a predetermined "on" time in which a series of electrical pulses of preset parameters is applied to the vagus branches, followed by a predetermined "off" time. One typical duty cycle comprises 30 seconds of stimulation and five minutes of no stimulation, repeated continuously. This cyclic stimulation program may initially result in little or no change in eating behavior. But it is expected that after a period of several days of such a chronic nerve stimulation regimen, the patient will experience a discernible loss of interest in heavy consumption of food. For example, mealtime consumption may extend over a considerably longer period of time than preoperatively, with smaller quantities of food intake separated by longer intervals of no consumption in the course of a single meal. Preferably the treatment regimen does not affect normal behavior in other aspects of the patient's life. A complete suspension of the stimulation regimen would be expected to result in a relatively rapid return (i.e., over a period of a few days) to the previous overeating behavior if there is relatively little restriction provided by band 30. However, if restriction if provided by lap band 30, the patient's eating behavior is expected to remain consistent with weight loss, as in prior art gastric band therapies.

The initiation of one or more stimulus signals (e.g., electrical, mechanical, and/or chemical) may result automatically according to the programmed duty cycle (in the case of electrical modulation) or by one of the modulation sub-units 4, 5, or 6. Alternatively, any of the foregoing stimulation sub-units may initiate therapy in response to manual activation of an output signal by the patient. The manual activation capability may be desirable in situations where the patient has an earnest desire to control his or her eating behavior, but because of a lack of sufficient will power or self-control to refrain from overeating, in the absence of measures described herein for inducing the feeling of satiety by neurostimulation. Manual activation capability is preferably additional to automatic, preset or programmed initiation. This option is especially desirable for counteracting or diminishing an instant urge to eat and/or to induce a feeling of satiety.

When two or three stimulation modes are used, the different modes of stimulating signals may be applied either synchronously or asynchronously, each mode preferably administered in the form of a series of pulses applied intermittently to one or more target areas according to a predetermined on/off duty cycle. The intermittent application is preferably chronic, rather than acute. However, both continuous application and acute application using one or more stimulation modes are contemplated for some treatment regimens. Acute application of stimulating signals via one or more stimulation modes during a customary mealtime, or from a short time preceding and/or following the mealtime, according to the patient's circadian cycle, may be effective in some cases.

In still another variation of treatment, a stimulating signal may be applied to one nerve or target area that is different from the stimulating signal applied to another target area contacted by band 30. The different stimulating signals may be of the same mode (e.g., electrical) but having different pulse parameters. Alternatively, the different stimulating signals may be of different modes (e.g., mechanical pressure and chemical) and the pulse parameters may be similar or different. For example, electrical stimulation according to a first parameter set (i.e., settings for current amplitude, frequency, pulse width, and duty cycle) may be applied to the anterior vagus nerve and electrical stimulation according to a second parameter set may be applied to the posterior vagus nerve in the esophagus/stomach area.

Electrical Modulation. With respect to the electrical stimulus mode, an implanted pulse generator sends an electrical pulse, or a series of pulses, to one or more stimulation electrode 36 of implanted band 30. The pulse generator 4 emits electrical stimuli in the form of electrical pulses defined by programmable parameters. The current amplitude is preferably programmed to be less than about 6 mA, and in any case is held below the retching level of the patient, as determined by the healthcare provider at the time the implant procedure and initial setup of the assembly are performed as described above. Adjustments to the programming parameters of the pulse generator 4 may be made at any time over the course of treatment so as to diminish or eliminate patient nausea, or to increase efficacy or reduce any undesired side effects. Preferably, the pulse width is set to a value not exceeding about 1500 μs, the pulse period (frequency) is set at about 10-250 Hertz (Hz), more preferably 20-30 Hz, with output current ranging from 1.0 to 8.0 mA. The treatment regimen includes alternating instances of stimulation and no stimulation, with the period of no stimulation preferably having a duration (length) less than about 100 times the length of the stimulation period in the alternating sequence (i.e., the on/off duty cycle is less than about 1:100, more preferably 1:1.8). These electrical and timing parameters of the stimulating signal used for electrical mode stimulation are merely exemplary, and it will be understood that different time and electrical parameters may be selected depending on the particular patient being treated and the judgment of the healthcare provider. All such variations are considered to be within the scope of the present invention.

As discussed in U.S. Pat. No. 5,263,480, vagal stimulation generates afferent and efferent action potentials on the vagus nerve, and the nerve signals between the brain and the stomach are carried primarily by the small C fibers which may become refractory if stimulated at high frequency (for example, 50 Hz or higher at high current amplitudes and/or duty cycles) for more than a period of 30 to 60 seconds. Therefore, in the present electrical stimulation mode, a strategy for inhibiting or blocking this C-fiber information is to stimulate at high frequencies (e.g., 250 Hz) with on-time of, say, 300 seconds and off-time of about 20 seconds. This sequence would be repeated for the interval of time that control (blocking of the C-fiber information) is desired to be exercised. Alternatively, because C fibers become refractory if stimulated for a sufficiently long period, another strategy would be to continuously stimulate the C fibers to render them refractory and thereby block the nerve signals between the brain and the esophagus/stomach. The signals of interest are believed to be conducted principally if not solely on the C fibers. These fibers are slow to conduct compared to the A and B fibers, but the slower response is acceptable here. Thus, the programming of stimulation parameters which block undesired C fiber vagalactivity while allowing faster A and/or B fiber pulses.

Mechanical Modulation. Stimulation of a target vagus nerve may also be achieved electromechanically or electrohydraulically. Although the effect upon the vagus nerve occurs through mechanical pressure, these two methods are provided in very different ways. Electromechanical stimulation of the nerve is provided by causing an electromechanical member 34 (e.g., a vibrator element such as a piezoelectric piston) to rapidly vibrate, preferably by moving radially outwardly and then inwardly on band 30. This produces oscillating mechanical stimulation against the target area and the underlying nerve(s).

In electrohydraulic mode, modulation is provided much more slowly. Band adjustment controller 7 withdraws saline or another suitable fluid from pressure fluid reservoir 12 and sends the fluid to an expandable cavity, balloon or other expansion member in band 30, in response to programmed instructions in band adjustment controller 7 or in response to signals from external programming system 10. As a result, pressure is applied to the treatment site to stimulate a target nerve. Subsequently, a quantity of fluid is removed from the fluid cavity or expansion member of band 30 and returned to reservoir 12, allowing band 30 to relax the pressure on the treatment site, and cease the stimulation of the nerve. These actions, in which the ring diameter of band 30 is constricted and then dilated in a rhythmic manner to stimulate a nerve, provide relatively low frequency stimulation as compared to the electrical stimulation described above. Essentially, electrohydraulic mode is similar to continuous adjustment (tightening and loosening) of the band 30.

Chemical Modulation. Chemical stimulation of target gastric nerves that project off of the anterior and posterior vagus nerves is preferably achieved by infusing an excitatory drug or chemical into the target area via one or more outlet ports 38, in accordance with the therapy algorithm programmed in pump 8. For example, an activating drug or chemical is withdrawn from reservoir 16 by pump 8, and delivered to the nerve through one or more outlet ports 38 as predetermined measured bursts in a repeating or rhythmic manner. A suitable activating chemical or drug is one that is known to cause an increase in the electrical discharge rate of a nerve. Alternatively, or additionally, if the pump 8 includes circuitry for receiving and processing a signal transmitted by telemetry, a burst of drug or chemical may be released from outlet 38 in response to such signal. Over the course of the treatment, as the supply of drug or chemical in reservoir 16 is depleted, it may be refilled or replaced with another drug or chemical, via percutaneous injection into port 18.

Using one or more of the three available modalities for stimulating the vagus/gastric nerves of the lower esophagus and/or upper stomach, with or without constricting the stomach to restrict food intake and slow down emptying of the stomach, the obese patient is expected to experience a decreased urge to eat and/or a feeling of satiety, which will result in desirable weight loss. After the desired weight loss has been achieved, the clinician may modify the programmed therapy algorithm to establish a treatment regimen and eating pattern that is appropriate for maintaining the patient's present reduced body weight. After establishing that the desired weight range for the patient, the system may continue to be used to enable the patient to maintain a desired weight, or it may be surgically removed via laparotomy.

Although certain preferred embodiments and methods of treating obesity through vagal modulation according to the invention have been described herein, it will be apparent to those skilled in the field from a consideration of the foregoing description that variations and modifications of such embodiments, methods and techniques may be made without departing from the true spirit and scope of the invention.

What is claimed is:

1. A system for treating an eating disorder by electrical stimulation of a vagus nerve of the patient in a manner to induce an afferent action potential on the nerve, comprising:
    an implantable gastric band having an inner periphery for contacting at least a portion of the patient's gastrointestinal tract innervated by said vagus nerve, said gastric band comprising a plurality of electrodes for electrical communication with said at least a portion of the gastrointestinal tract and said vagus nerve, wherein said plurality of electrodes is used for both sensing and inducing afferent action potentials; and
    a pulse generator coupled to said plurality of electrodes and configured to generate a test electrical signal to be applied to said plurality of electrodes, and also configured to select which of said electrode(s) are to be used to induce said action potentials based on detection of an afferent action potential in said nerve induced by said test electrical signal and sensed by at least one said electrode, and further configured to provide an electrical stimulation signal to at least said selected electrode sufficient to induce an exogenous afferent action potential on said vagus nerve of the patient while permitting transmission of native action potentials on said nerve.

2. The system of claim 1, wherein said electrical stimulation signal comprises a pulsed electrical signal and said pulse generator comprises a controller for defining said pulsed electrical signal by a plurality of stimulation parameters selected from the group consisting of a voltage magnitude, a current magnitude, a frequency, a pulse width, an on-time and an off-time.

3. The system of claim 2 wherein said controller is capable of independently addressing each of said plurality of electrodes to deliver said electrical signal to any combination of said plurality of electrodes.

4. The system of claim 1, wherein said eating disorder is selected from the group consisting of obesity, bulimia nervosa, and anorexia nervosa.

5. The system of claim 1 wherein said electrical stimulation signal is configured to generate both exogenous afferent and exogenous efferent action potentials on the vagus nerve of the patient while permitting said transmission of native action potentials on said nerve.

6. The system of claim 1 wherein said implantable gastric band further comprises an adjustment element that allows said band to be non-invasively and post-operatively adjusted in size to vary a constriction applied to said at least a portion of the gastrointestinal tract.

7. The system of claim 6 wherein said adjustment element comprises at least one inflatable balloon member.

8. A method of treating an eating disorder by electrical stimulation of a vagus nerve of the patient to induce afferent action potentials on said nerve, comprising:
    surgically coupling an implantable gastric band to at least a portion of the patient's gastrointestinal tract innervated by said vagus nerve, wherein said implantable gastric band comprises a plurality of electrodes;
    generating an electrical test signal and applying said electrical test signal to at least two of said plurality of electrodes;
    identifying at least a first electrode of said plurality of electrodes that senses a test action potential or is nearest to an electrode that senses said test action potential on said vagus nerve induced by said electrical test signal;
    generating an electrical stimulation signal configured to induce an exogenous afferent action potential on said vagus nerve of the patient without blocking native action potentials on said nerve;
    applying said electrical stimulation signal to said identified first electrode to induce said exogenous afferent action potential on said nerve while permitting transmission of native action potentials on said nerve, to treat said eating disorder comprising obesity, bulimia or anorexia nervosa.

9. The method of claim 8 further comprising the step of providing a pulse generator, said step of generating an electrical stimulation signal comprising generating an electrical stimulation signal using said pulse generator.

10. The method of claim 9 wherein said step of providing a pulse generator comprises providing an implantable pulse generator and a lead, said method further comprising the step of coupling said pulse generator to said plurality of electrodes with said lead.

11. The method of claim 9 wherein said step of providing a pulse generator comprises providing an external pulse generator that is inductively coupled to said plurality of electrodes.

12. The method of claim 9 wherein said step of providing a pulse generator comprises providing a pulse generator having a controller capable of independently addressing each of said plurality of electrodes to deliver said electrical signal to any combination of said plurality of electrodes.

13. The method of claim 8 wherein said implantable gastric band comprises a plurality of stimulation electrodes and a plurality of sensing electrodes, said method further comprising sensing said induced action potentials on said nerve using said sensing electrodes.

14. The method of claim 13, wherein said plurality of sensing electrodes are located above said plurality of stimulating electrodes on said band.

15. The method of claim 8 wherein said step of generating an electrical signal comprises generating a pulsed electrical signal defined by a plurality of stimulation parameters including at least a current magnitude, a frequency, and a pulse width.

16. The method of claim 8, wherein said eating disorder is selected from the group consisting of obesity, bulimia nervosa, and anorexia nervosa.

17. The method of claim 8 comprising inducing said exogenous afferent action potentials and inducing exogenous efferent action potentials on said vagus nerve while permitting transmission of native action potentials on said nerve.

18. The method of claim 8 wherein said identifying comprises identifying said first electrode and a second electrode, wherein said first electrode senses a first test action potential or is nearest to an electrode that senses said first test action potential on the patient's anterior vagus nerve, and said second electrode senses a second test action potential or is nearest to an electrode that senses said second test action potential on the patient's posterior vagus nerve.

19. The method of claim 18 wherein inducing exogenous afferent action potentials on said vagus nerve comprises inducing exogenous afferent action potentials on both said anterior vagus nerve and said posterior vagus nerve while permitting transmission of native action potentials on said nerves.

20. The method of claim 8 wherein said step of providing an implantable gastric band comprises providing a band having an adjustment element.

21. The method of claim 20 wherein said adjustment element is configured for non-invasive actuation, said method further comprising the step of post-operatively and non-invasively adjusting the size of the gastric band to vary a constriction of said at least a portion of the gastrointestinal tract.

22. The method of claim 20, wherein said at least a portion of the patient's gastrointestinal tract comprises at least a portion of the lower esophagus, cardia, esophageal/cardia junction, and cardia/fundus junction.

23. The method of claim 8, wherein said step of generating an electrical stimulation signal comprises generating an electrical stimulation signal in response to a patient command.

24. The method of claim 23, wherein said patient command is provided by a magnetic signal from said patient.

25. The method of claim 8 wherein said plurality of electrodes are capable of both sensing and inducing action potentials on said nerve.

* * * * *